US011596753B2

(12) United States Patent
Sherman et al.

(10) Patent No.: US 11,596,753 B2
(45) Date of Patent: *Mar. 7, 2023

(54) AUTOMATIC PATIENT VENTILATOR SYSTEM AND METHOD

(71) Applicant: Zoll Medical Corporation, Chelmsford, MA (US)

(72) Inventors: Leslie H. Sherman, Denville, NJ (US); George Beck, Mendham, NJ (US); Douglas R. Connelly, Rockaway, NJ (US); John W. Freeman, East Orange, NJ (US)

(73) Assignee: ZOLL Medical Corporation, Chelmsford, MA (US)

( * ) Notice: Subject to any disclaimer, the term of this patent is extended or adjusted under 35 U.S.C. 154(b) by 1027 days.

This patent is subject to a terminal disclaimer.

(21) Appl. No.: 14/933,446

(22) Filed: Nov. 5, 2015

(65) Prior Publication Data

US 2016/0051780 A1 Feb. 25, 2016

Related U.S. Application Data

(63) Continuation of application No. 10/893,156, filed on Jul. 16, 2004, now Pat. No. 9,180,266.

(Continued)

(51) Int. Cl.
*A61M 16/00* (2006.01)
*A61M 16/12* (2006.01)
(Continued)

(52) U.S. Cl.
CPC .... *A61M 16/0057* (2013.01); *A61M 16/0003* (2014.02); *A61M 16/0051* (2013.01);
(Continued)

(58) Field of Classification Search
CPC .............. A61M 16/00; A61M 16/0003; A61M 16/0057; A61M 16/0063; A61M 16/024;
(Continued)

(56) References Cited

U.S. PATENT DOCUMENTS 4,459,982 A * 7/1984 Fry ..................... A61M 16/022
128/204.23
5,239,994 A * 8/1993 Atkins .............. A61M 16/0096
128/204.18

(Continued)

OTHER PUBLICATIONS

Medical Dictionary, "Ventilation" entry, "High-frequency ventilation" sub-entry, 2019. (Year: 2019).*

(Continued)

*Primary Examiner* — Justine R Yu
*Assistant Examiner* — Jacqueline M Pinderski
(74) *Attorney, Agent, or Firm* — The Webb Law Firm

(57) ABSTRACT

Ventilator enables operator to enter into the microprocessor estimate of a patient's individual characteristic, such as weight, which the microprocessor uses to control delivered tidal volume and other parameters to match the patient. The operator can select one of several ventilator operational modes (intube, mask, CPR). Sensors input data to the microprocessor to maintain parameter optimizations and accuracy. Visual/audible alarms and tools activate when one or more parameters exceed or fail to exceed predetermined values for patient's weight. Manual over-ride is available. The ventilator has a quick start capability in which the operator turns on power, selects the automatic operating mode, enters patient's characteristic, selects control option starting automatic ventilation of proper volumes inhalation/ exhalation periods, pressure, and oxy-air mixture.

40 Claims, 14 Drawing Sheets

Related U.S. Application Data

(60) Provisional application No. 60/488,013, filed on Jul. 17, 2003.

(51) Int. Cl.
*A61H 31/00* (2006.01)
*A61M 16/10* (2006.01)
*A61M 16/08* (2006.01)
*A61M 16/20* (2006.01)

(52) U.S. Cl.
CPC ......... *A61M 16/024* (2017.08); *A61H 31/005* (2013.01); *A61M 16/0063* (2014.02); *A61M 16/0808* (2013.01); *A61M 16/107* (2014.02); *A61M 16/1045* (2013.01); *A61M 16/125* (2014.02); *A61M 16/204* (2014.02); *A61M 16/205* (2014.02); *A61M 2016/0027* (2013.01); *A61M 2016/0039* (2013.01); *A61M 2016/1025* (2013.01); *A61M 2205/18* (2013.01); *A61M 2205/3358* (2013.01); *A61M 2205/502* (2013.01); *A61M 2205/581* (2013.01); *A61M 2205/583* (2013.01); *A61M 2205/6081* (2013.01); *A61M 2205/702* (2013.01)

(58) Field of Classification Search
CPC .............. A61M 16/0051; A61M 16/20; A61M 16/201; A61M 16/202; A61M 16/203; A61M 16/204; A61M 16/205; A61M 16/125; A61M 2205/583; A61M 2205/502; A61M 2205/3358; A61M 2205/581; A61M 2205/18; A61M 2205/70; A61M 2205/702; A61M 2016/003; A61M 2016/0039
See application file for complete search history.

(56) References Cited

U.S. PATENT DOCUMENTS

| | | | |
|---|---|---|---|
| 5,320,093 A | 6/1994 | Raemer | |
| 5,540,220 A * | 7/1996 | Gropper | A61M 16/024 |
| | | | 128/204.21 |
| 5,645,053 A | 7/1997 | Remmers et al. | |
| 5,692,497 A * | 12/1997 | Schnitzer | A61M 16/0051 |
| | | | 128/204.21 |
| 5,752,509 A * | 5/1998 | Lachmann | A61M 16/024 |
| | | | 128/203.12 |
| 5,915,380 A * | 6/1999 | Wallace | A61M 16/0051 |
| | | | 128/204.21 |
| 5,915,381 A * | 6/1999 | Nord | A61M 16/08 |
| | | | 128/204.23 |
| 6,000,396 A * | 12/1999 | Melker | A61M 16/206 |
| | | | 128/204.21 |
| 6,099,481 A | 8/2000 | Daniels et al. | |
| 6,155,257 A * | 12/2000 | Lurie | A61H 31/005 |
| | | | 128/204.18 |
| 6,512,938 B2 | 1/2003 | Claure et al. | |
| 6,581,600 B2 | 6/2003 | Bird | |
| 6,587,726 B2 | 7/2003 | Lurie et al. | |
| 6,796,305 B1 * | 9/2004 | Banner | A61B 5/0205 |
| | | | 128/204.21 |
| 6,840,240 B1 * | 1/2005 | Berthon-Jones | A61M 16/00 |
| | | | 128/204.18 |
| 7,174,891 B2 * | 2/2007 | Lurie | A61H 31/005 |
| | | | 128/204.23 |
| 9,180,266 B1 * | 11/2015 | Sherman | A61M 16/024 |
| 2001/0033074 A1 * | 10/2001 | Aoki | B60R 21/01532 |
| | | | 280/735 |
| 2006/0201503 A1 | 9/2006 | Breen | |

OTHER PUBLICATIONS

Babbs, C. F., and K. B. Kern "Optimum compression to ventilation ratios in CPR under realistic, practical conditions: A physiological and mathematical analysis." (2002). Resuscitation, 54(2), 147-157. (Year: 2002).*

Owen-Thomas, J. B., O. A. Ulan, and P. R. Swyer. "The Effect of Varying Inspiratory Gas Flow Rate on Arterial Oxygenation during IPPV in the Respiratory Distress Syndrome." (1968). British Journal of Anesthesia, 40, pp. 493-502. (Year: 1968).*

Sten, Rubertsson, Ake Grenvik, Vitas Zemgulis, Lars Wiklund. "Systemic Perfusion Presure and Blood Flow Before and After Administration of Epinephrine during Experimental Cardiopulmonary Resuscitation". (1995). Critical Care Medicine, vol. 23, Issue 12. (Year: 1995).*

Vendrinne, Jean-Marc, Serge Duperret, Francois Decaillot, Pierre Gratadour, Jean Motin. "Reports of Investigation; Haemodynamic Changes Induced by Two I:E Ratios: A Transoeesophageal Echocardiographic Study". (1997). Canadian Journal of Anesthesia 44: 4, pp. 354-359. (Year: 1997).*

Circulation 2000; 102:1-95, ECC Guidelines, Part 6: Advanced Cardiovascular Life Support.

Foley et al., "Managing the Airway in the Critically Ill Patient", Critical Care Clinics, Jul. 2000, vol. 16, No. 3.

Pepe et al., "Action Sequence for layperson cardiopulmonary resuscitation", Annals of Emergency Medicine, Apr. 2001, vol. 37, No. 4.

* cited by examiner

TABLE 1 - DEFAULT VALUES (AT PATIENT WEIGHT SETTING)

| WT. (kg) | RATE (bpm) | I-TIME AT 1:3 I:E RATIO | TIDAL VOLUME (ml) | MINUTE VOLUME | PRESSURE RELIEF/ ALARM SETPOINT (cmH2O) | WT. (kg) | RATE (bpm) | I-TIME AT 1:3 I:E RATIO | TIDAL VOLUME (ml) | MINUTE VOLUME | PRESSURE RELIEF/ ALARM SETPOINT (cmH2O) |
|---|---|---|---|---|---|---|---|---|---|---|---|
| 8 | 30 | 0.50 | 64 | 1920 | 20 | 50 | 13 | 1.20 | 451 | 5647 | 35 |
| 9 | 29 | 0.52 | 69 | 1988 | 20 | 51 | 12 | 1.24 | 459 | 5508 | 35 |
| 10 | 28 | 0.54 | 73 | 2056 | 20 | 52 | 12 | 1.24 | 468 | 5616 | 35 |
| 11 | 26 | 0.57 | 79 | 2075 | 20 | 53 | 12 | 1.25 | 477 | 5724 | 35 |
| 12 | 26 | 0.58 | 84 | 2166 | 20 | 54 | 12 | 1.25 | 486 | 5832 | 35 |
| 13 | 24 | 0.62 | 93 | 2258 | 20 | 55 | 12 | 1.25 | 495 | 5940 | 35 |
| 14 | 24 | 0.64 | 100 | 2350 | 20 | 56 | 12 | 1.25 | 504 | 6048 | 35 |
| 15 | 23 | 0.66 | 107 | 2441 | 20 | 57 | 12 | 1.25 | 513 | 6156 | 35 |
| 16 | 22 | 0.68 | 114 | 2533 | 20 | 58 | 12 | 1.25 | 522 | 6264 | 35 |
| 17 | 22 | 0.69 | 123 | 2660 | 20 | 59 | 12 | 1.25 | 531 | 6372 | 35 |
| 18 | 22 | 0.70 | 126 | 2716 | 20 | 60 | 12 | 1.25 | 540 | 6480 | 35 |
| 19 | 21 | 0.72 | 135 | 2808 | 20 | 61 | 12 | 1.25 | 549 | 6588 | 35 |
| 20 | 21 | 0.72 | 139 | 2899 | 20 | 62 | 12 | 1.25 | 558 | 6696 | 35 |
| 21 | 20 | 0.75 | 149 | 2991 | 20 | 63 | 12 | 1.25 | 567 | 6804 | 35 |
| 22 | 20 | 0.75 | 153 | 3082 | 20 | 64 | 12 | 1.25 | 576 | 6912 | 35 |
| 23 | 19 | 0.78 | 164 | 3174 | 20 | 65 | 12 | 1.25 | 585 | 7020 | 35 |
| 24 | 19 | 0.77 | 168 | 3266 | 20 | 66 | 12 | 1.25 | 594 | 7128 | 35 |
| 25 | 19 | 0.81 | 181 | 3357 | 25 | 67 | 12 | 1.25 | 603 | 7236 | 35 |
| 26 | 19 | 0.81 | 185 | 3449 | 25 | 68 | 12 | 1.25 | 612 | 7344 | 35 |
| 27 | 19 | 0.80 | 190 | 3540 | 25 | 69 | 12 | 1.25 | 621 | 7452 | 35 |
| 28 | 18 | 0.84 | 204 | 3632 | 25 | 70 | 12 | 1.25 | 630 | 7560 | 35 |
| 29 | 18 | 0.84 | 208 | 3724 | 25 | 71 | 12 | 1.25 | 639 | 7668 | 35 |
| 30 | 18 | 0.84 | 213 | 3815 | 25 | 72 | 12 | 1.25 | 648 | 7776 | 35 |
| 31 | 18 | 0.83 | 217 | 3907 | 25 | 73 | 12 | 1.25 | 657 | 7884 | 35 |
| 32 | 18 | 0.85 | 226 | 3998 | 25 | 74 | 12 | 1.25 | 666 | 7992 | 35 |
| 33 | 18 | 0.85 | 232 | 4090 | 25 | 75 | 12 | 1.25 | 675 | 8100 | 35 |
| 34 | 18 | 0.85 | 237 | 4182 | 25 | 76 | 12 | 1.25 | 684 | 8208 | 35 |
| 35 | 17 | 0.87 | 248 | 4273 | 35 | 77 | 12 | 1.25 | 693 | 8316 | 35 |
| 36 | 17 | 0.89 | 260 | 4365 | 35 | 78 | 12 | 1.25 | 702 | 8424 | 35 |
| 37 | 16 | 0.92 | 272 | 4456 | 35 | 79 | 12 | 1.25 | 711 | 8532 | 35 |
| 38 | 16 | 0.94 | 285 | 4548 | 35 | 80 | 12 | 1.25 | 720 | 8640 | 35 |
| 39 | 16 | 0.97 | 299 | 4640 | 35 | 81 | 12 | 1.25 | 729 | 8748 | 35 |
| 40 | 15 | 0.99 | 313 | 4731 | 35 | 82 | 12 | 1.25 | 738 | 8856 | 35 |
| 41 | 15 | 1.02 | 329 | 4823 | 35 | 83 | 12 | 1.25 | 747 | 8964 | 35 |
| 42 | 14 | 1.05 | 345 | 4914 | 35 | 84 | 12 | 1.25 | 756 | 9072 | 35 |
| 43 | 14 | 1.09 | 363 | 5006 | 35 | 85 | 12 | 1.25 | 765 | 9180 | 35 |
| 44 | 14 | 1.09 | 369 | 5098 | 35 | 86 | 12 | 1.25 | 774 | 9288 | 35 |
| 45 | 13 | 1.12 | 388 | 5189 | 35 | 87 | 12 | 1.25 | 783 | 9396 | 35 |
| 46 | 13 | 1.12 | 395 | 5281 | 35 | 88 | 12 | 1.25 | 792 | 9504 | 35 |
| 47 | 13 | 1.16 | 415 | 5372 | 35 | 89 | 12 | 1.25 | 801 | 9612 | 35 |
| 48 | 13 | 1.16 | 422 | 5464 | 35 | 90 | 12 | 1.25 | 810 | 9720 | 35 |
| 49 | 13 | 1.20 | 444 | 5556 | 35 | 91 | 12 | 1.25 | 819 | 9828 | 35 |

FIG. 5

TABLE 1 - DEFAULT VALUES (AT PATIENT WEIGHT SETTING), (CONT'D)

| WT. (kg) | RATE (bpm) | I-TIME AT 1:3 I:E RATIO | TIDAL VOLUME (ml) | MINUTE VOLUME VOLUME | PRESSURE RELIEF/ ALARM SETPOINT (cmH2O) | WT. (kg) | RATE (bpm) | I-TIME AT 1:3 I:E RATIO | TIDAL VOLUME (ml) | MINUTE VOLUME VOLUME | PRESSURE RELIEF/ ALARM SETPOINT (cmH2O) |
|---|---|---|---|---|---|---|---|---|---|---|---|
| 92 | 12 | 1.25 | 828 | 9936 | 35 | 102 | 12 | 1.25 | 918 | 11016 | 35 |
| 93 | 12 | 1.25 | 837 | 10044 | 35 | 103 | 12 | 1.25 | 927 | 11124 | 35 |
| 94 | 12 | 1.25 | 846 | 10152 | 35 | 104 | 12 | 1.25 | 936 | 11232 | 35 |
| 95 | 12 | 1.25 | 855 | 10260 | 35 | 105 | 12 | 1.25 | 945 | 11340 | 35 |
| 96 | 12 | 1.25 | 864 | 10368 | 35 | 106 | 12 | 1.25 | 954 | 11448 | 35 |
| 97 | 12 | 1.25 | 873 | 10476 | 35 | 107 | 12 | 1.25 | 963 | 11556 | 35 |
| 98 | 12 | 1.25 | 882 | 10584 | 35 | 108 | 12 | 1.25 | 972 | 11664 | 35 |
| 99 | 12 | 1.25 | 891 | 10692 | 35 | 109 | 12 | 1.25 | 981 | 11772 | 35 |
| 100 | 12 | 1.25 | 900 | 10800 | 35 | 110 | 12 | 1.25 | 990 | 11880 | 35 |
| 101 | 12 | 1.25 | 909 | 10908 | 35 | | | | | | |

NOTES:
1. QUICK-START MODE = ASSIST CONTROL VENTILATION
2. CLOSED LOOP CONTROL WILL ADJUST V_T (DOWN) TO MAINTAIN PIP < PRESSURE RELIEF SETPOINT AND ADJUST RATE (UP SLIGHTLY FROM DEFAULT VALUE (MAX 20)) TO MAINTAIN Vmin.
3. MAXIMUM Wt. SHALL NOT CAUSE Vt TO EXCEED 1500ml (RATE, I-TIME, AND ml/Kg CONSTANTS REMAIN THE SAME).

CHILD VALUES

FIG. 6

AUTOMATIC PATIENT VENTILATOR SYSTEM AND METHOD

RELATED APPLICATIONS

This application is a continuation application of U.S. application Ser. No. 10/893,156, filed Jul. 16, 2004, which claims priority to U.S. Provisional Application No. 60/488, 013, filed Jul. 17, 2003, both of which are incorporated herein by reference in their entirety.

BACKGROUND

The present invention relates to patient breathing assist systems and, more particularly, to such systems that are microprocessor-controlled patient ventilator systems and methods of control and operation therefor.

Designers have improved human patient ventilators in the last ten years by including microprocessors to control various functions of the ventilator equipment. See, for example, U.S. Pat. Nos. 5,692,497 and 6,512,938. Standard microprocessor controlled ventilators operate in two or three different modes, depending upon the nature of the injury or illness giving rise for patient's need for assisted breathing, and the operators selection of one or more specific mode settings. In addition, the microprocessor can respond to various sensors to modify air-oxygen mixture, flow rates, and other parameters pursuant to protocols stored in the microprocessor unit.

But these conventional ventilators are not free of technical problems. For example, conventional microprocessor controlled ventilators can force delivery of the wrong tidal volumes, flow rates, gas mixtures, inspiratory pressure, inspiratory/expiratory ratio, or other operating parameters. In addition, if the conventional system delivers the wrong quantity or at the wrong rate, the operator must use visual patient reaction to sense and determine the sufficiency of or incorrect setting of the system. These shortcomings of conventional microprocessor controlled ventilators may cause delay in establishing normal patient breathing which can lead to patient injury or death.

In addition, manual ventilation is currently the standard of care in pre-hospital setting. This form of ventilation requires that a rescue operator, usually having low level skill and training, squeeze a self-inflating bag connected to an indwelling tube or simultaneously holds a mask in place to deliver breathing gas to the patient. Studies have shown that, in order to minimize breathing gas leakage, this process often requires two rescuers, one to hold the mask firmly in place and the other to squeeze the bag. This technique obliges the rescuer to guess: how often to squeeze the bag, how quickly to squeeze the bag, and for how long to squeeze the bag. This process is repeated each time a manual breath is delivered.

In the pre-hospital care setting, patients receive ventilations rendered by emergency medical technicians (EMTs), paramedics, police officers, and firemen. Each of these personnel categories has limited mechanical ventilation skills and is not clinically qualified to make most operator control settings, which are normally dependent upon multiple cycles of in-hospital tests to ascertain. The self-inflating bag, described above, and the automatic transport ventilator (ATV) are the two most popular devices available for breathing gas delivery in the pre-hospital care environment. At the present time, ATV's are automatic only in the sense that they can automatically and repeatedly cycle from off to on. The operator is responsible for making control settings based on his/her perception of what he/she thinks the patient needs and within the gas delivery/functionality limitations of the ATV. Depending upon the clinical expertise of the caregiver, which is generally minimal, these control settings are little more than a "best guess". Furthermore, the ATV has no mechanism for self-correction or ability to provide assurance that the mechanical ventilations delivered to the patient actually represents the ATV settings. Although the literature reports ATV's as being robust devices and superior to the self-inflating bag, most hospital medical directors require their field personnel to manually ventilate patients, because this mode will pose the least threat from pressure-related injury due to incorrect ATV settings.

Mechanical ventilation is used in pre-hospital or clinic. In the hospital or clinic, mechanical ventilation is used therapeutically to wean a patient to that point where mechanical breathing support is no longer required. In all clinical environments, there exists a need to have mechanical ventilation capability without the need for significant input and attention from the operator.

In the hospital/clinic environment, patients receive ventilations rendered by nurses, physicians, respiratory therapists, and anesthesiologists. Each of these personnel categories has some degree of manual and/or mechanical ventilation skills, ranging from minimal to considerable, and traditionally subordinates to that member of the clinical team that is most proficient in ventilating the patient. The self-inflating bag, described earlier, and battery-powered critical care ventilators are the two most popular adjuncts available for breathing gas delivery in the hospital/clinic setting. The self-inflating bag is subject to the same limitations described earlier and is typically used during emergency procedures or short intra-hospital transports. The less-rugged critical care ventilator can be used during emergency procedures but is used more typically where longer periods of continuous use in specialized therapeutic care are required. More importantly, the critical care ventilator is dependent upon the availability of a highly skilled operator to assure that its control settings continuously represent the patient's immediate needs, safety, and comfort level. Incorrect settings place the patient at risk from hypo or hyperventilation and pressure-related injury to sensitive tissue.

A common need has always existed, in both the pre-hospital care and hospital/clinic environments for a mechanical ventilator that can be quickly and easily deployed and is simple-to-use by low skill level personnel. Thus, it should provide emergency ventilatory care intervention to facilitate its use rather than present a therapeutic ventilatory care interface that is impractical for the application and is likely to intimidate the operator or permit patient injury.

In the pre-hospital care setting, such a device would be routinely used by personnel, regardless of their level of training, and allow them to automatically provide safe, consistent and repeatable ventilations. In field settings, it would prove invaluable, as it is commonly known that injuries from mass destruction (fires, explosions, chemical clouds, etc.) specifically involve patients' respiratory systems leading to incapacitation and death if emergency ventilatory care is not provided within a short period of time.

In the hospital/clinic setting, a similar need exists to provide immediate care to many patients who've become the victims of mass destruction affecting the respiratory system. The problem is the same as that encountered in pre-hospital settings. The location of use is different but the solution remains the same, whereas the use of conventional microprocessor controlled ventilators or manual adjuncts will limit the amount of patients/victims served, cause critical delays in providing needed ventilatory intervention, and lend itself to further patient injury or death.

SUMMARY OF THE INVENTION

It is an object to provide a microprocessor controlled ventilator that solves the foregoing technical problems, provides other and further benefits and advantages, and provides a faster start, more automatic and more reliable ventilation assistance to patients in need of such assistance than conventional or known mechanical units of this type, and enable these benefits with lesser skilled or trained operators. In addition, a preferred embodiment lends itself to implementation in a small lightweight package with AC or, alternately, battery power for convenient portability, storage and in-field, ambulance and hospital usage.

One exemplary embodiment of a ventilator system, according to the principles of the present invention, includes a subassembly for delivering to the patient air or oxygen or a mixture thereof. Unlike conventional systems and methods, the present system enables the operator to enter into the microprocessor storage register the operator's estimate of a patient's individual characteristic or factor, such as weight. This approximate weight factor is then used automatically by the microprocessor in the protocol, algorithm, or stored table look-up for the particular mode of ventilator operation selected by the operator. For example, the microprocessor will control the delivered tidal volume and control other parameters to match the specific patient's individual characteristic, such as the patient's weight, during the specific ventilator operational mode.

Another object of the invention is to provide such ventilators that use the entered individual characteristic in combination with one or more sensor inputs to the microprocessor to control one or more of the various system parameters for the specific mode of system operation.

A further object of the present invention is to provide such ventilators in which the microprocessor chip (MC) controls one or more visual and/or audible alarms when one or more parameters exceed or fail to exceed predetermined values for the individual characteristic and specific mode operation of the system.

Yet a further object of the invention is to provide a ventilator with quick start capability in which the operation turns on power, selects the automatic operating mode (intubate/non-intubate, 100% oxygen/oxy-air mixture), enters the individual characteristic, and selects a control option to start automatic ventilation of proper volumes inhalation/exhalation periods, and oxy-air mixture.

Advantageously, a low-skill level operator can more effectively operate the present ventilator because of the few data and mode selection inputs to the present ventilator.

Yet another object of the present invention is to provide an automatic ventilator that can be used during and to assist an operator during CPR. The inventive ventilator here includes a metronome and audio and/or visual indicator to indicate the patient's heart beat. It also sequences the patient ventilation during operator pauses in chest pressure.

Further objects and aspects of the present invention include new and better methods of providing breathing assistance to patients applicable in a wide variety of injury, illness, or aged conditions.

BRIEF DESCRIPTION OF THE DRAWINGS

Other and further features, objects, and benefits provided by the present invention shall become apparent with the following description of an exemplary embodiment when taken in view of the appended drawings in which.

Figure 1:
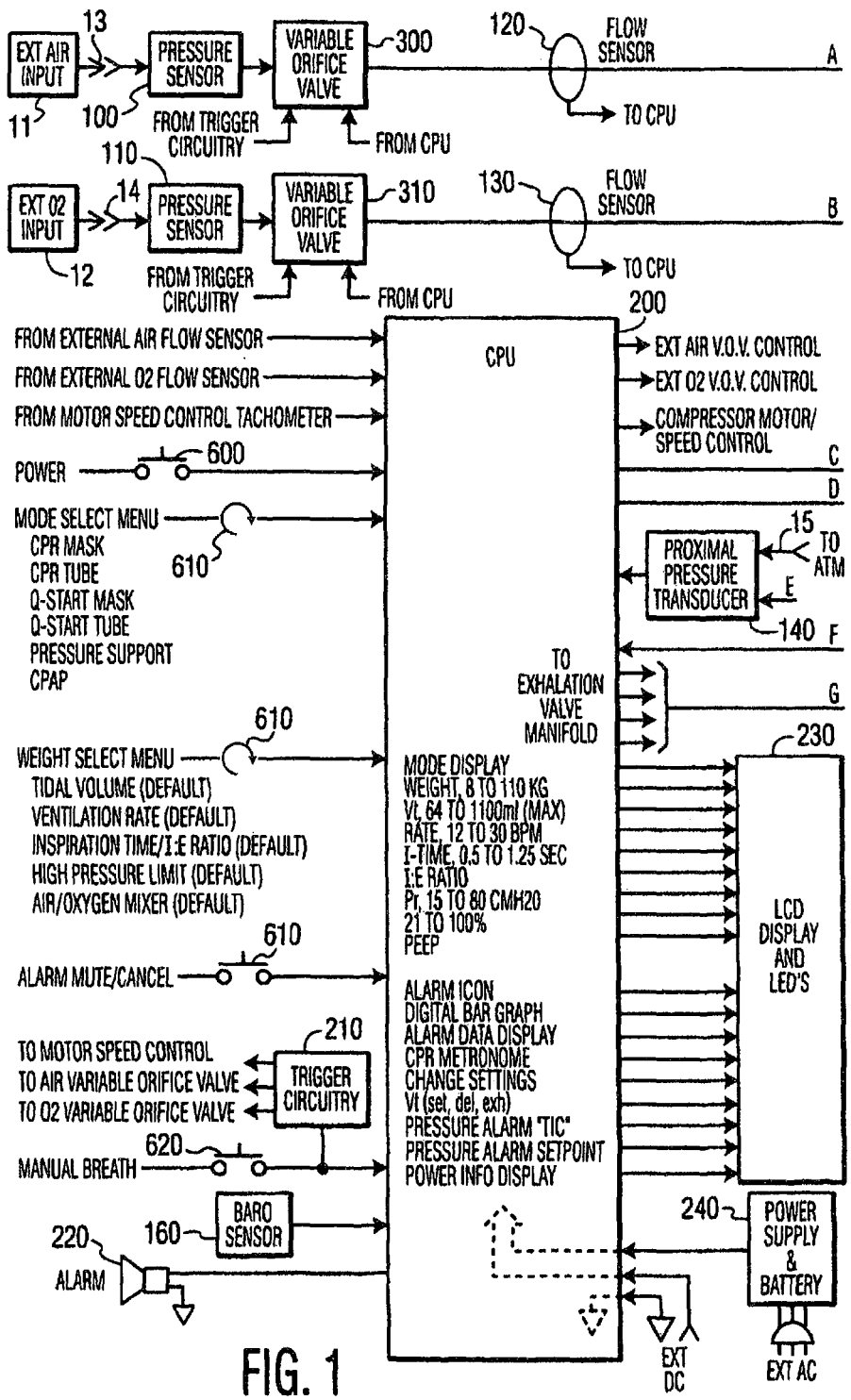
FIG. 1 is a schematic and block diagram of part of an exemplary embodiment according to the present invention.
Figure 2:
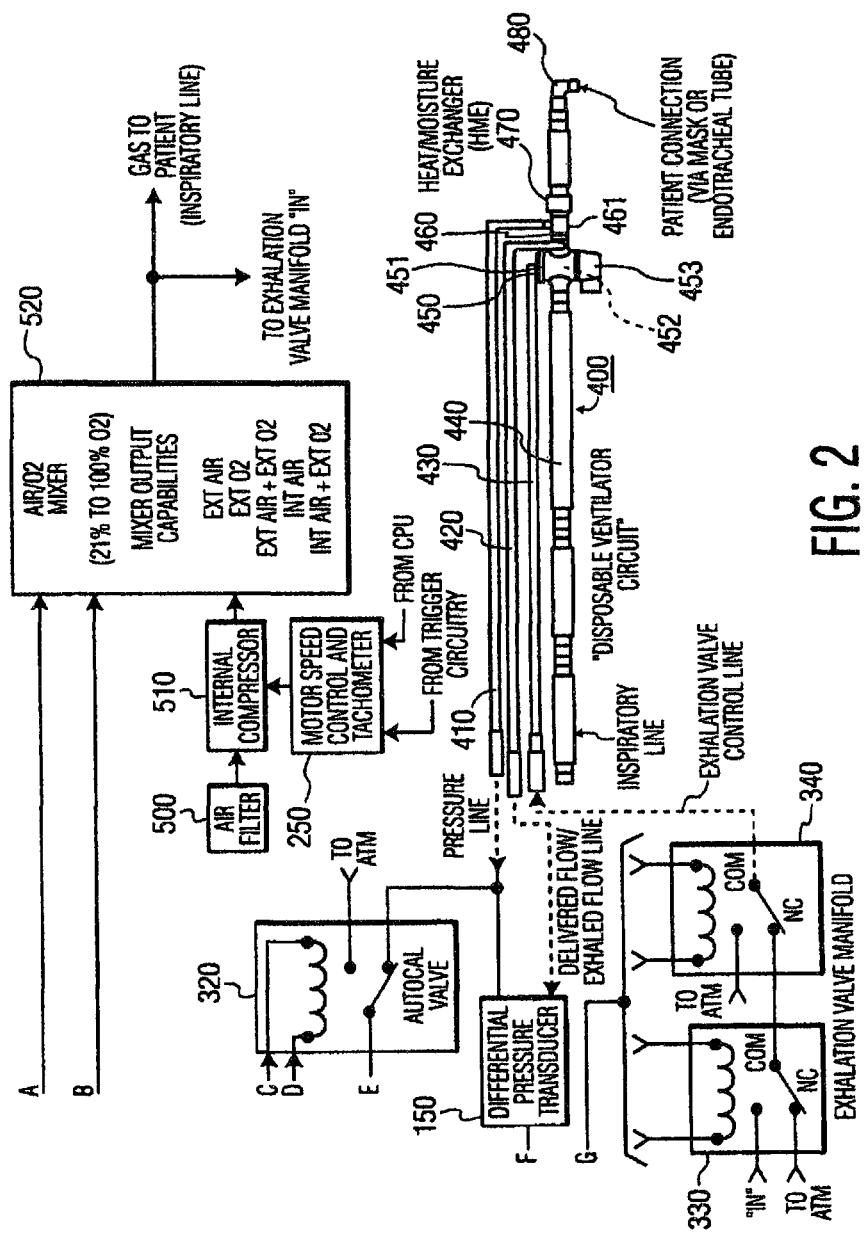
FIG. 2 is similar to FIG. 1 showing a different part of the exemplary embodiment.

It will be understood that FIGS. 1 and 2 should be read together to form a complete diagram. Letters A-G, respectively, identify common lines on each FIGS. 1 and 2.

Figure 3:
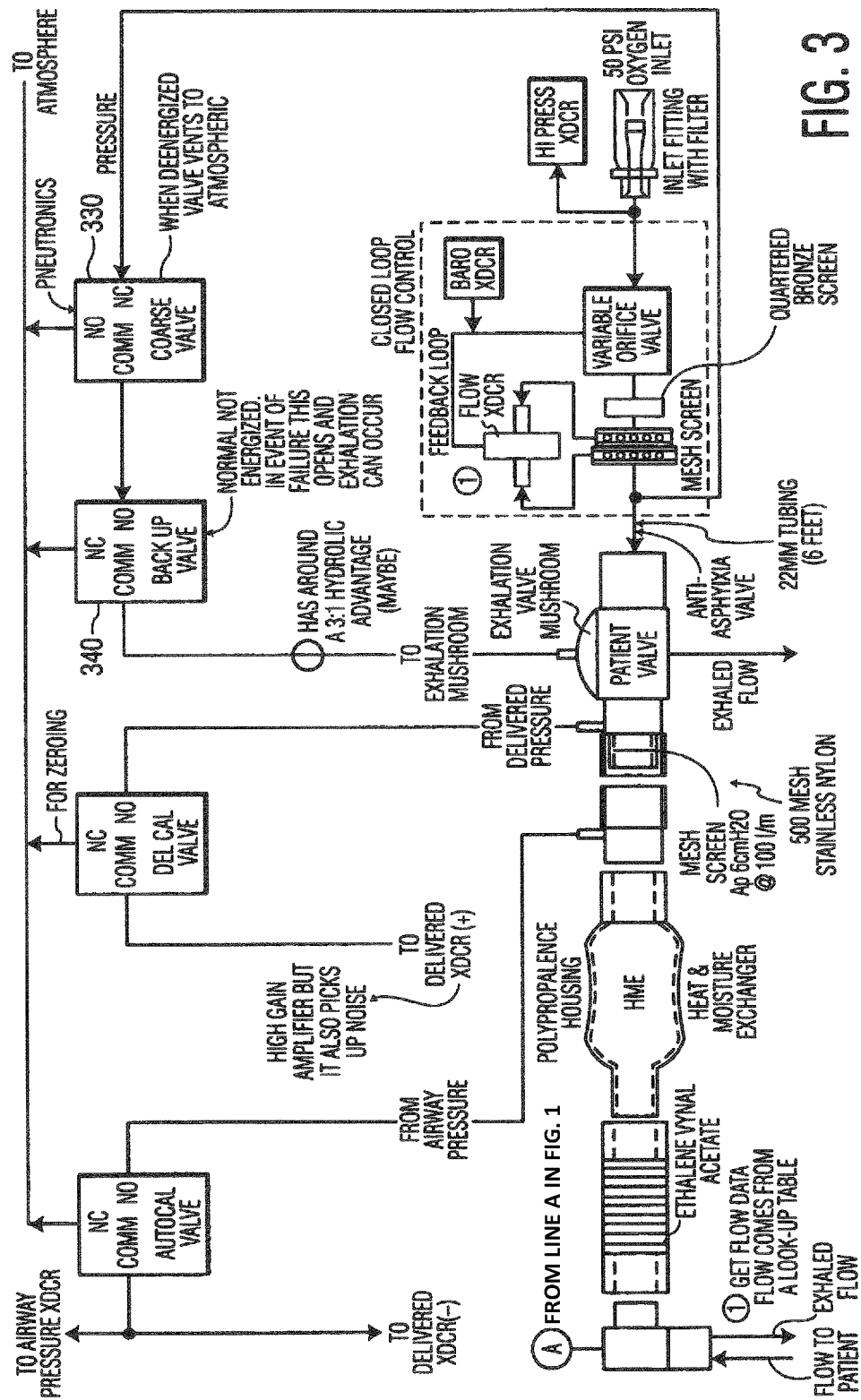

FIG. 3 is a schematic diagram of an exemplary embodiment of the pneumatic circuit of the embodiment of FIGS. 1 and 2.

Figure 4:
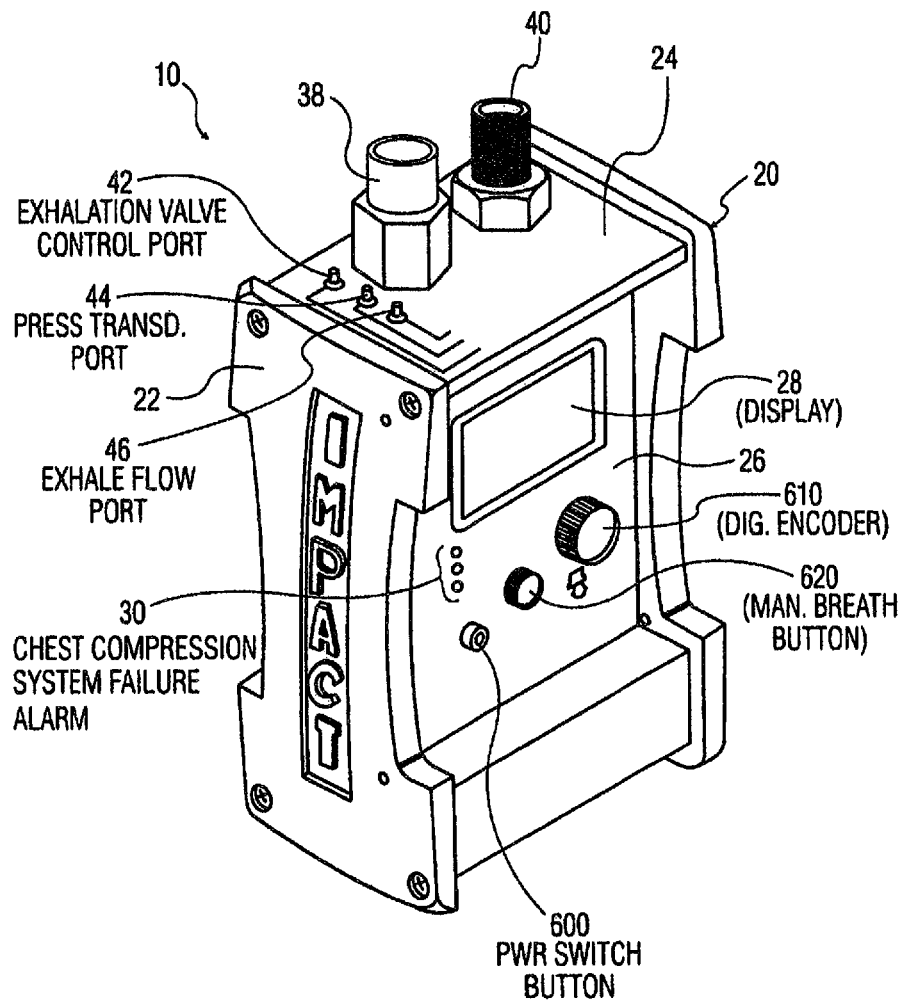

FIG. 4 is a perspective view of one exemplary housing and controls for the embodiment of FIGS. 1 and 2.

FIG. 5 is a table showing exemplary default ventilator settings based on Radford values and patient weight settings.

FIG. 6 is similar to FIG. 5 for child weight settings.

Figure 7:
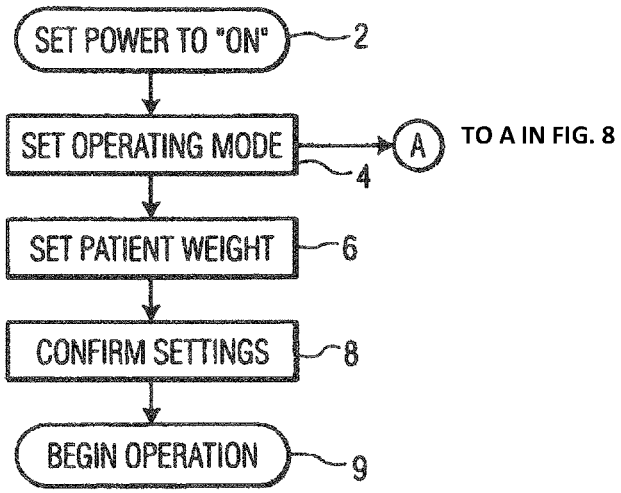

FIG. 7 is a flow diagram of an exemplary start-up method of the embodiment of FIGS. 1 and 2.

Figure 8:
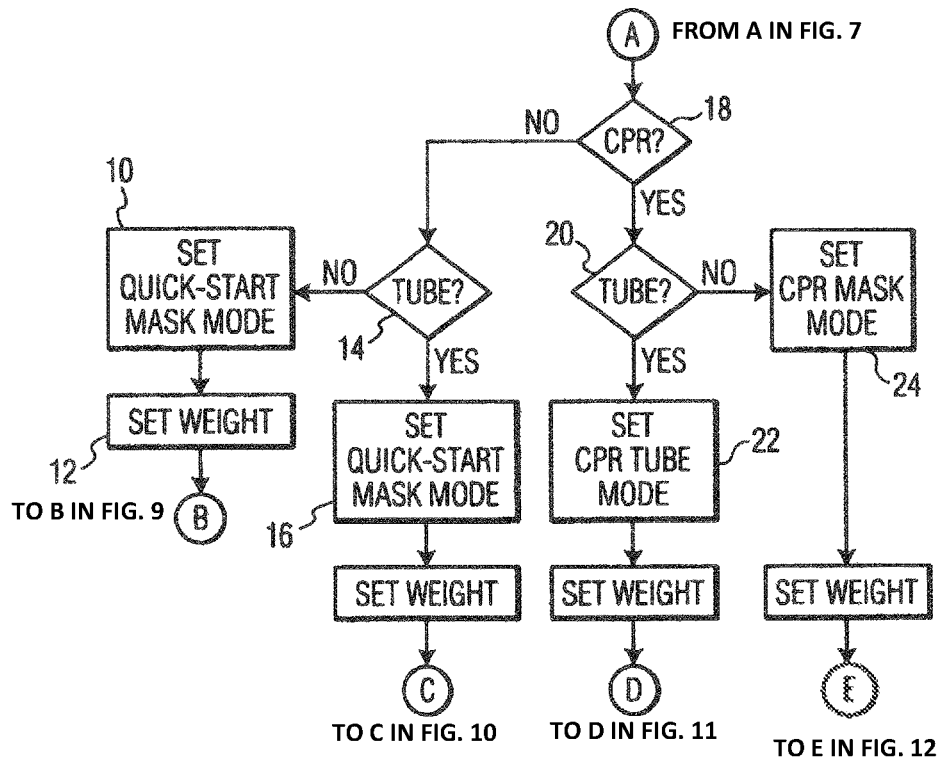

FIG. 8 is a flow diagram of an exemplary ventilation mode selection method of the embodiment of FIGS. 1 and 2.

Figure 9:
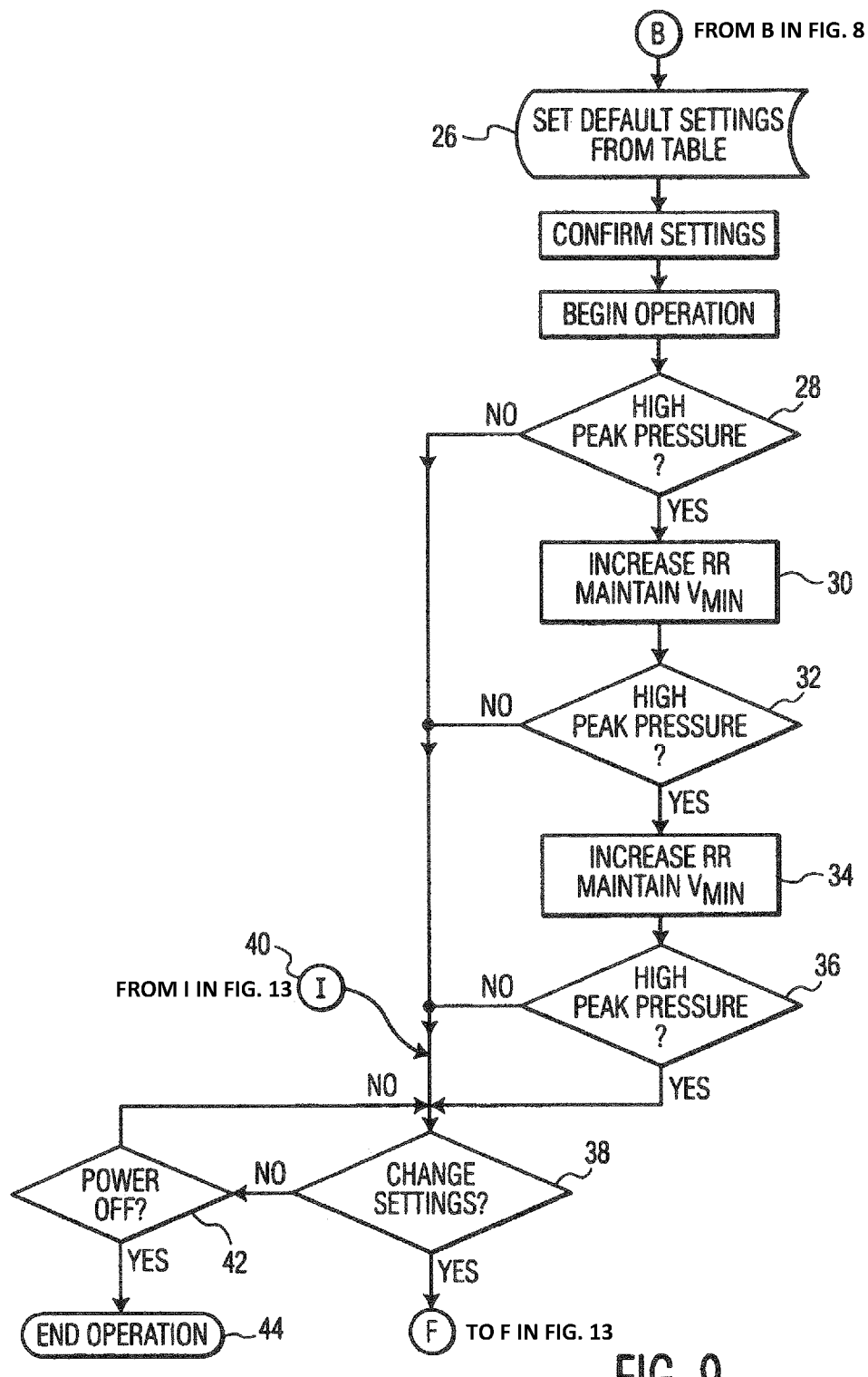

FIG. 9 is a flow diagram of an exemplary quick-start mask mode method of the embodiment of FIGS. 1 and 2.

Figure 10:
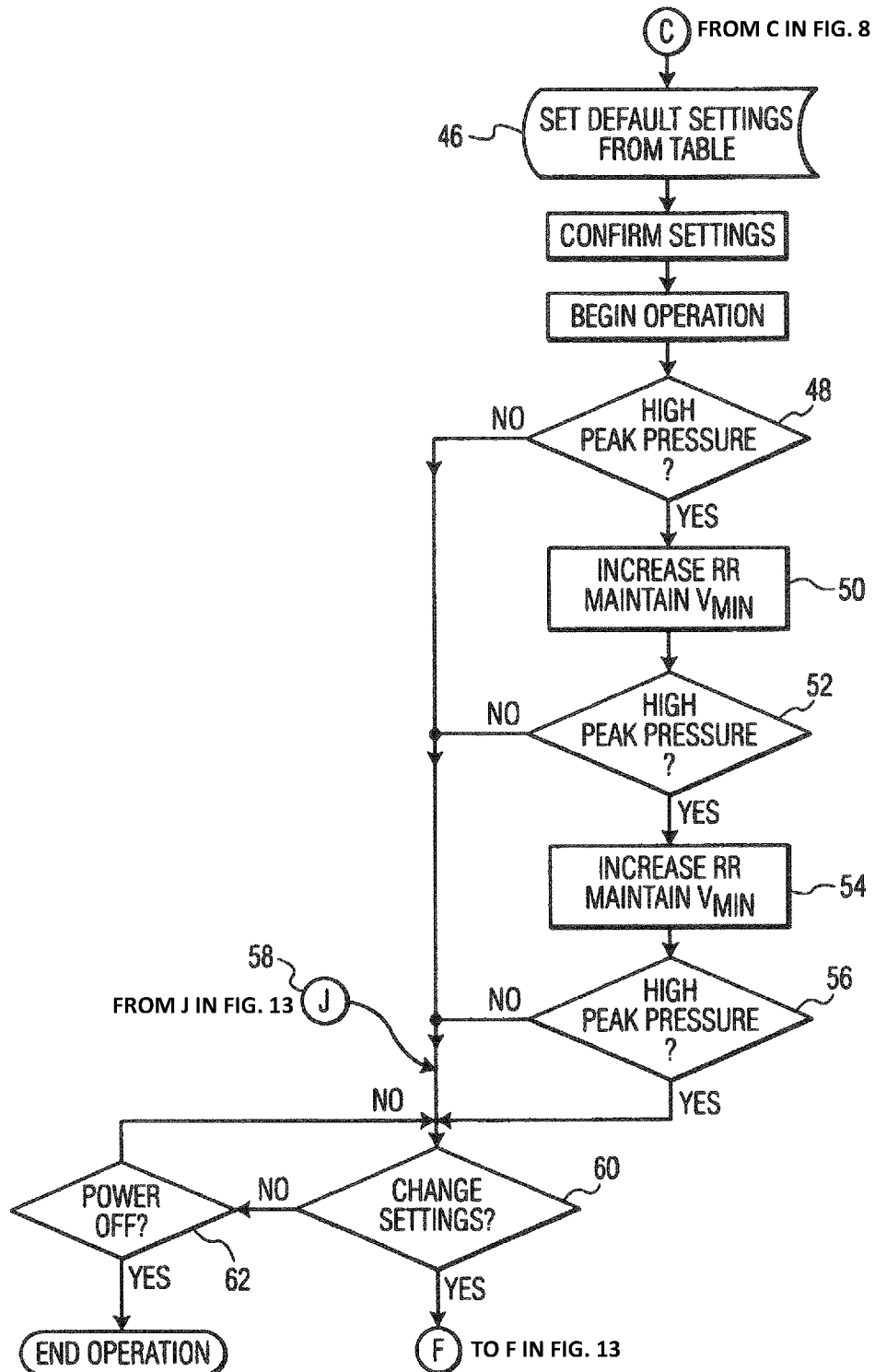

FIG. 10 is a flow diagram of an exemplary quick-start tube mode method of the embodiment of FIGS. 1 and 2.

Figure 11:
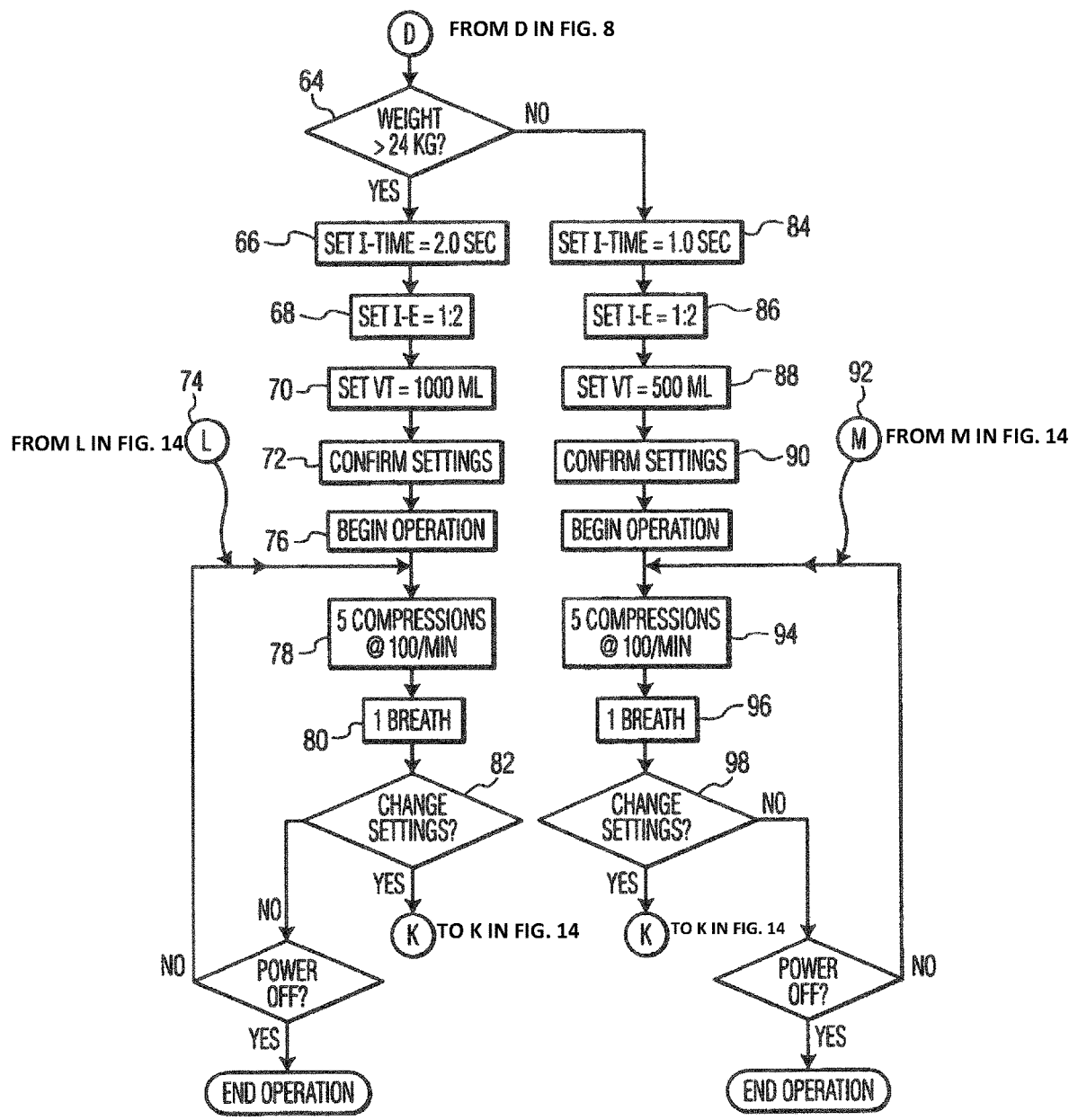

FIG. 11 is a flow diagram of an exemplary CPR tube mode method of the embodiment of FIGS. 1 and 2.

Figure 12:
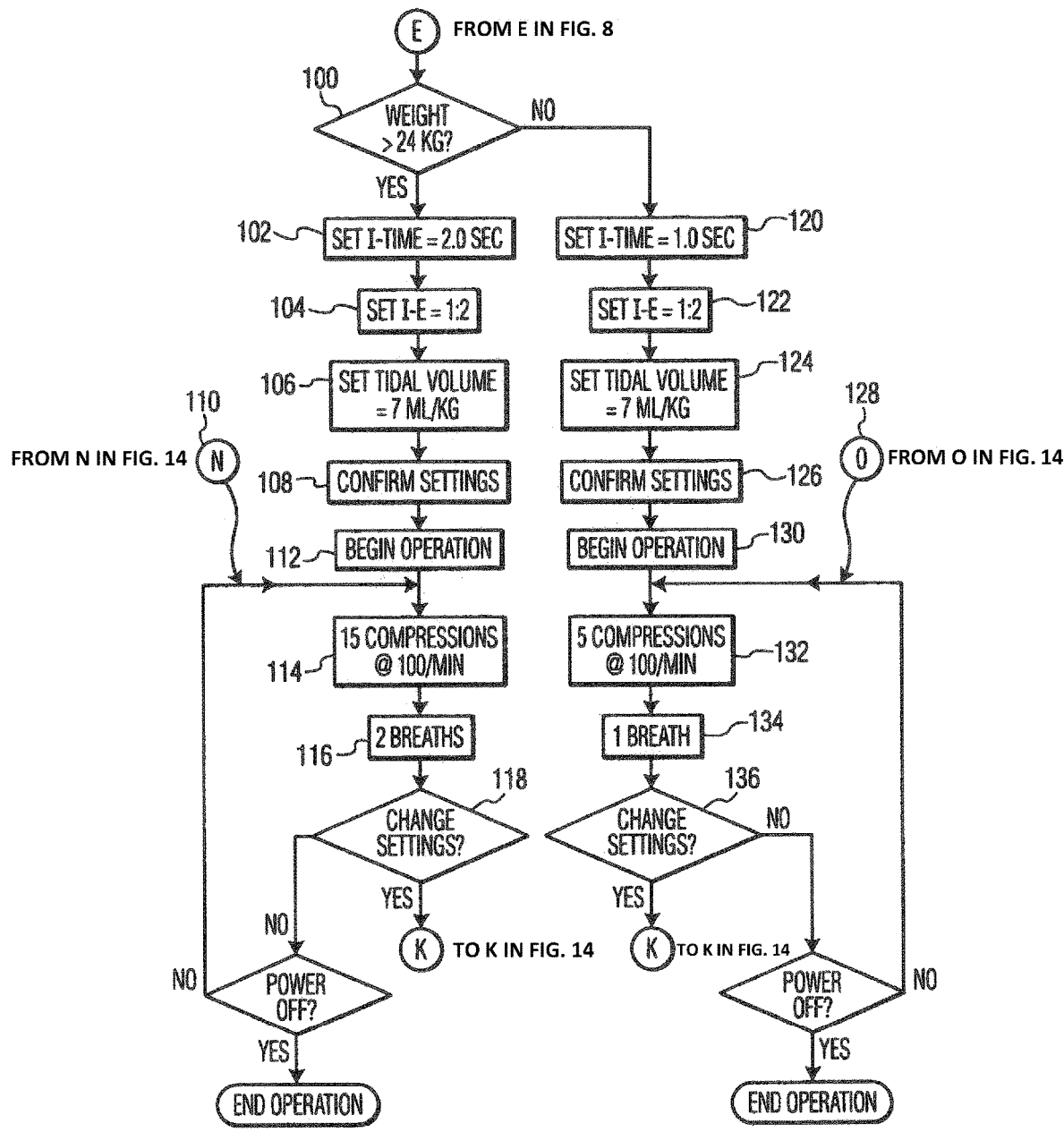

FIG. 12 is a flow diagram of an exemplary CPR mask mode method of the embodiment of FIGS. 1 and 2.

Figure 13:
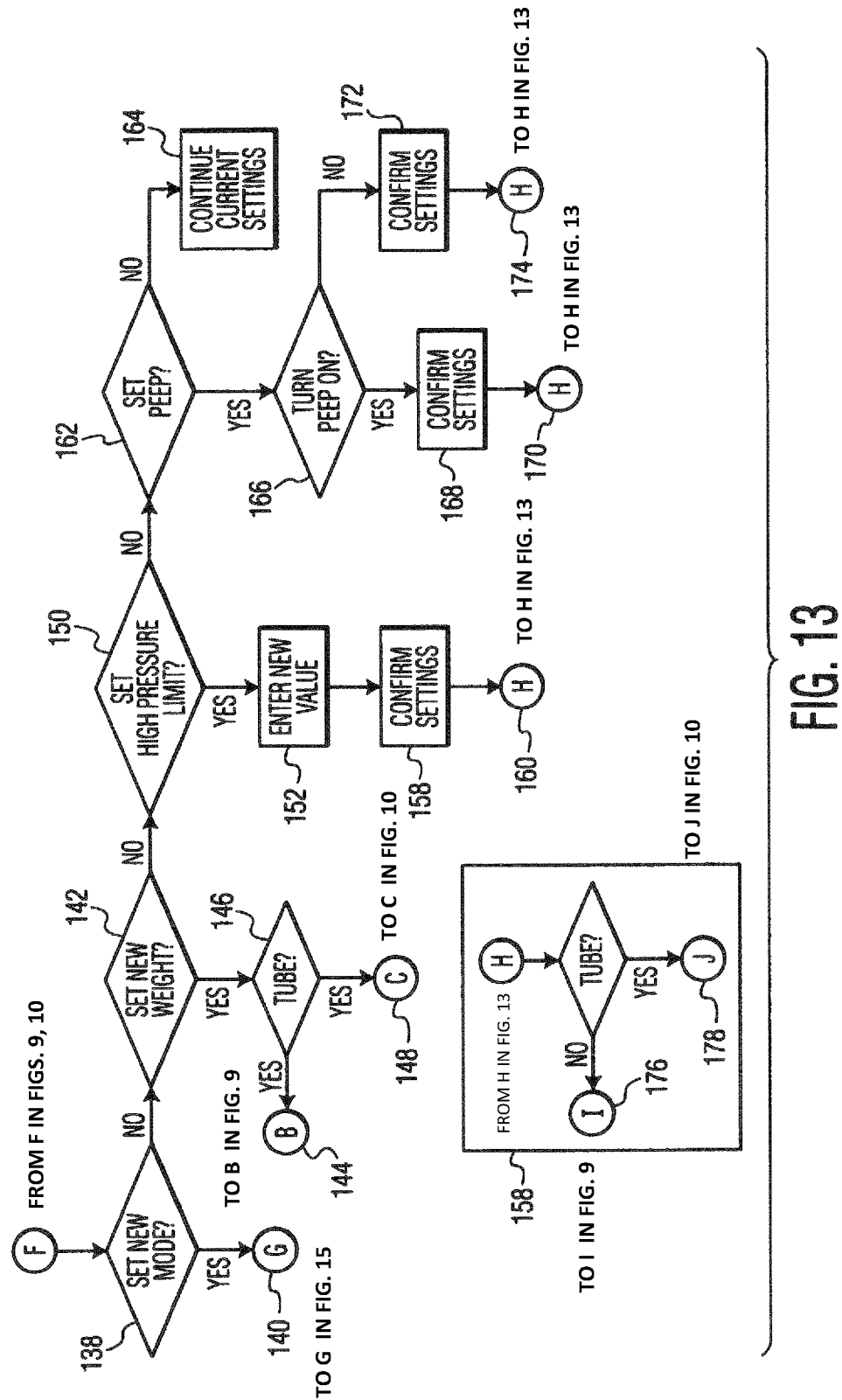

FIG. 13 is a flow diagram of an exemplary change settings for quick start mode method of the embodiment of FIGS. 1 and 2.

Figure 14:
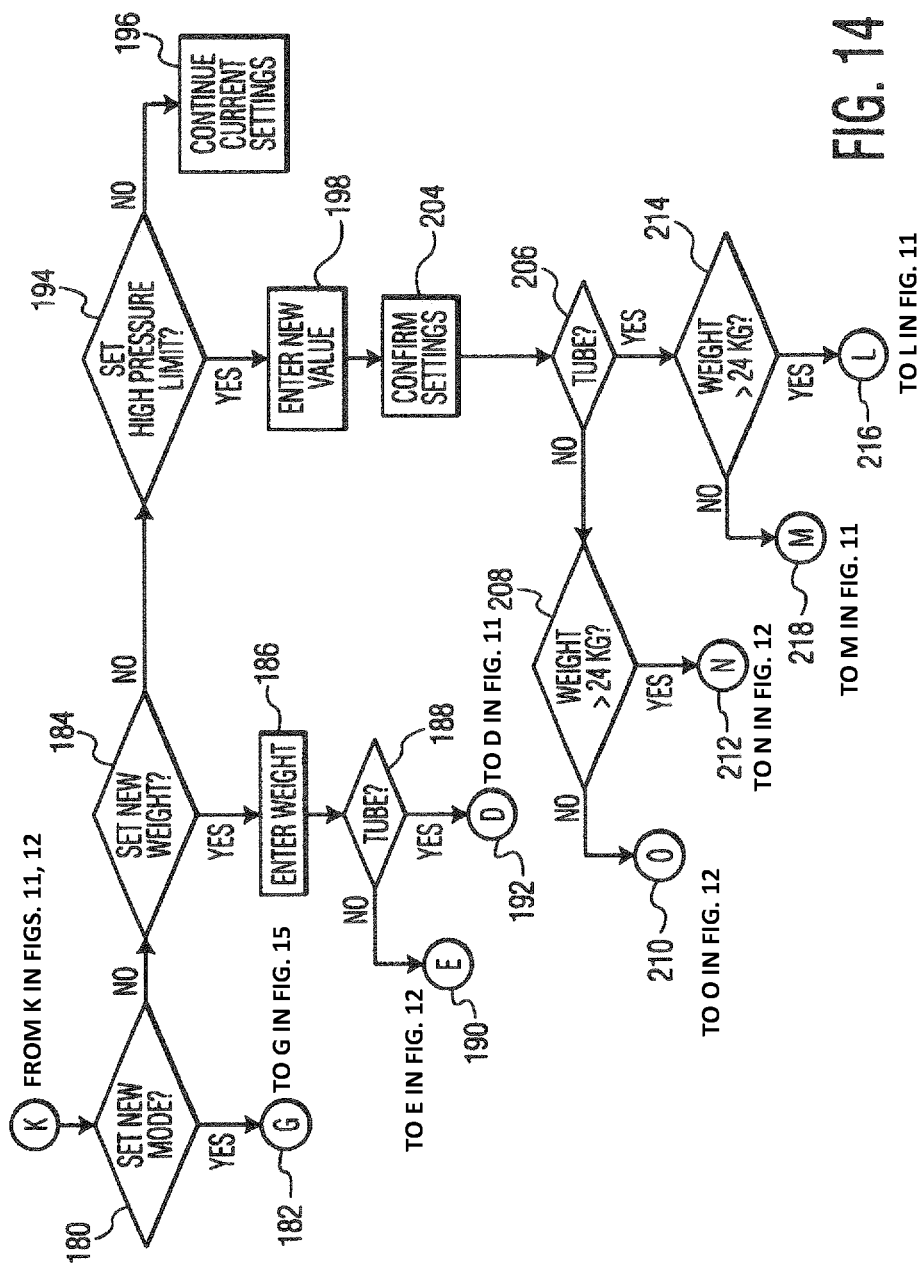

FIG. 14 is a flow diagram of an exemplary change settings in CPR modes method of the embodiment of FIGS. 1 and 2.

Figure 15:
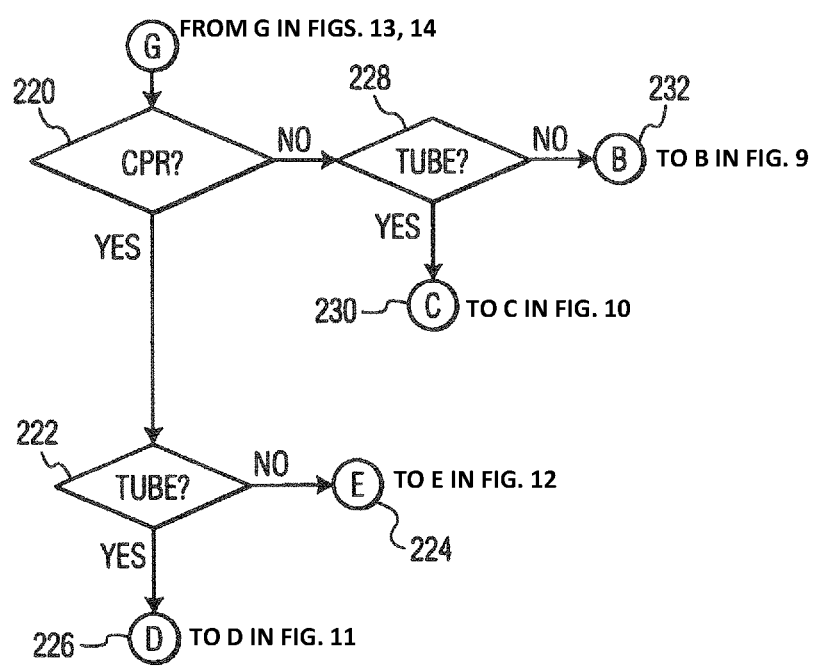

FIG. 15 is a flow diagram of an exemplary change settings/return to mode method of the embodiment of FIGS. 1 and 2.

DETAILED DESCRIPTION OF THE INVENTION

FIGS. 1 and 2 show one exemplary ventilation embodiment 10 according to the principles of the present invention. Elements and subassemblies of ventilator 10 shall now be described.

Sensors

Gaseous medical-grade air, e.g., from cylinder 11, is regulated to nominal 50-PSI through a pressure regulator or provided via an oil-less compressor with appropriate filter and regulator (not shown). Interconnection is made between the air source and ventilator's External Air Input Connector 13 by color-coded pressure hose and size-indexed fittings. Pressure is sensed continuously by pressure sensor transducer 100 and triggers the External Air Low/Fail Alarm audible/LED/message when pressure falls below the ventilator's external air alarm set point value, details of which are further described below.

Gaseous medical-grade oxygen, e.g., from cylinder 12, is regulated to nominal 50-PSI through a pressure regulator. Interconnection is made between the oxygen source and ventilator's External Oxygen Input Connector 14 by color-coded pressure hose and size-indexed fittings. Pressure is sensed continuously by a pressure sensor transducer 110 and triggers the Oxygen Low/Fail Alarm audible/LED/message when pressure falls below the ventilator's oxygen alarm set point value, as further described below.

External Air Flow Sensor 120 is part of a closed loop measurement and medical-grade air delivery sub-system that includes the External Air Flow Sensor 120, Variable Orifice Valve 300, Air/Oxygen Mixer 520, CPU 200, Differential Pressure Transducer 150, and Disposable Ventilator Circuit 400.

The External Air Flow Sensor 120 can be a pneumotach that consists of a differential pressure transducer; a fine mesh screen located between the transducer inputs and associated electronic circuitry. The sensor outputs the pressure drop signal across the mesh screen. The output signal is processed and quantified at the microprocessor 200 then compared to data contained within the ventilator's memory ("look-up table"). The look-up table data contains a gas flow value (calibrated for air) equivalent to each measured pressure drop over the ventilator's usable range. In use, the ventilator is preset to deliver a volume (set tidal volume) within an established time (inspiratory time) for a particular patient, as further described below. Based on the sensor's real-time measurements and flow equivalents, the microprocessor 200 makes on-the-fly aperture adjustments to the Variable Orifice Valve 300 to control flow and insure "delivered" volume equals "set" volume.

An External Oxygen Flow Sensor 130 is part of a closed loop measurement and oxygen delivery sub-system that includes the External Oxygen Flow Sensor 130, Variable Orifice Valve 310, Air/Oxygen Mixer 520, CPU 200, Differential Pressure Transducer 150 and Disposable Ventilator Circuit 400. The External Oxygen Flow Sensor 130 can be a pneumotach that consists of a differential pressure transducer; a fine mesh screen located between the transducer inputs and associated electronic circuitry. The sensor outputs the pressure drop signal across the mesh screen. The signal is processed and quantified at the microprocessor 200 then compared to data contained within the ventilator's memory ("look-up table). The look-up table data contains a gas flow value (calibrated for oxygen) equivalent to each measured pressure drop over the ventilator's usable range. In use, the ventilator is preset to deliver a volume (set tidal volume) within an established time (inspiratory time) for a particular patient. Based on the sensor's real-time measurements and flow equivalents, the microprocessor 200 makes on-the-fly aperture adjustments to the Variable Orifice Valve 310 to control flow and insure "delivered" volume equals "set" volume.

A Proximal Pressure Sensor 140 is a differential transducer. One input 15 is open to atmosphere and the other input is connected to Autocal Valve 320. The output of sensor 140 is to directed CPU 200.

At startup (power is set to "ON"), the microprocessor 200 performs a Self-Check. Self-Check is a series of diagnostic checks that the ventilator must successfully pass before regular operation is allowed to begin. One of these checks includes setting the pressure signal baseline to "zero" (the equivalent of local atmospheric pressure). Additionally, during operation, the ventilator performs automatic recalibrations at regular intervals to compensate for baseline drift or dramatic changes in altitude that would effect, or have affected, the zero baseline. The signal output of the Proximal Pressure Sensor 140 represents any offset that may exist between the input open to atmospheric pressure and pressure line input from the Ventilator Circuit 400 through the Autocal Valve 320.

The Differential Pressure Transducer 150 is part of a closed loop measurement and external air and oxygen delivery sub-system that includes the External Air Flow Sensor 120, Variable Orifice Valve 300, the External Oxygen Flow Sensor 130, Variable Orifice Valve 310, Air/Oxygen Mixer 520, CPU 200, Differential Pressure Transducer 150, and Disposable Ventilator Circuit 400. The Differential Pressure Transducer 150 is part of a pneumotach sensor that is created when a Disposable Ventilator Circuit's 400 Pressure Line 410 and Delivered Flow/Exhaled Flow Line 420 tubing are connected to their respective ventilator tube connectors. The opposite ends of the Pressure Line 410 and Delivered Flow/Exhaled Flow Line 420 tubing are attached to tube fittings located on either side of a fine mesh screen 460. The Differential Pressure Transducer 150 outputs the pressure drop signal across the mesh screen 460. The signal is processed and quantified at the microprocessor 200 then compared to data contained within the ventilator's memory ("look-up table"). The look-up table data contains a gas flow value (calibrated for air, air and oxygen mixtures, and oxygen) equivalent to each measured pressure drop over the ventilator's usable range. In use, the ventilator is preset to deliver a volume (set tidal volume) within an established time (inspiratory time) for a particular patient. The Differential Pressure Transducer's 150 real-time measurements allow the microprocessor 200 to "see" delivered flow during the inspiratory cycle, which, in turn, makes on-the-fly aperture adjustments to the respective Variable Orifice Valve 300 and 310 to insure "delivered" volume equals "set" volume.

A Baro Sensor 160 provides barometric pressure information to the CPU 200. Gas density changes with altitude and affects the accuracy of readings measured by each of the ventilator's pneumotachs. To automatically compensate when necessary, the Baro Sensor 160 continuously monitors barometric pressure so that correction factors can be added to pneumotach measurements to maintain accuracy.

Electronic and Electrical Components

CPU 200 processes signal information sent from its switches, control, power and sensor inputs. It also sends control signals to the Variable Orifice Valve 300 and 310, Autocal Valve 320, Exhalation Valve Manifold 330 and 340 and Motor Speed Control and Tachometer 250. Sends settings, alarm, and measurement information to an LCD 230 for display purposes and alarm signals to an Alarm Piezo 220 for annunciation. One example of a suitable CPU is 800552-P80C552-IBA, manufactured by Philips Semiconductors.

A Trigger Circuit 210 allows a "measured" breath to be delivered each time a Manual Breath Pushbutton 620 is pressed. A Manual Breath is equal in volume and duration to current ventilator settings for "set" tidal volume and inspiratory time for a particular patient. The Alarm Piezo 220 is activated each time an alarm is triggered and muted for a predetermined period, or cancelled, when an Alarm Mute/Cancel Pushbutton 610 is pressed. The Alarm Piezo 220 is also used to emit a "chirp" acknowledging each time pushbutton switches 610 and 620 are pressed and each time the CPR Metronome indicates chest compression is required.

The LCD Display and LED's 230 present visual, text and graphical information to the operator. LCD information includes: ventilator settings, alarm by name and associated message, power status, charging status, pressure measurement and metronome Off/On. LED information includes: Chest Compression, Alarm and System Failure.

Power Supply 240 circuitry provides ventilator operating and/or battery charging power. In addition, the Power Supply 240 circuitry provides internal battery and external power status signals to the microprocessor 200 displayed in the LCD 230. The Battery 240 provides operating power independent from an external power source.

The Motor Speed Control and Tachometer 250 circuit controls an Internal Compressor's 510 motor speed. This insures a reliable airflow source to meet "set" volume requirements. A separate input allows the Motor Speed Control and Tachometer 250 to become activated for one breath each time the Manual Breath Pushbutton 620 is pressed.

Pneumatics

Ventilator 10 pneumatic apparatus will now be described. The External Air Variable Orifice Valve 300 is part of a closed loop measurement and medical-grade air delivery sub-system that includes the External Air Flow Sensor 120, Variable Orifice Valve 300, Air/Oxygen Mixer 520, CPU 200, Differential Pressure Transducer 150 and Disposable Ventilator Circuit 400. Based on real-time measurements and flow equivalents made by the External Air Flow Sensor 120 and Differential Pressure Transducer 150, both described earlier, the microprocessor 200 can make on-the-fly aperture adjustments to the Variable Orifice Valve 300 to control flow and insure "delivered" volume equals "set" volume.

The External Oxygen Variable Orifice Valve 310 is part of a closed loop measurement and medical-grade air delivery system that includes the External Oxygen Flow Sensor 130, Variable Orifice Valve 310, Air/Oxygen Mixer 520, CPU 200, Differential Pressure Transducer 150 and Disposable Ventilator Circuit 400. Based on real-time measurements and flow equivalents made by the External Oxygen Flow Sensor 130 and Differential Pressure Transducer 150, both described earlier, the microprocessor 200 can make on-the-fly aperture adjustments to the Variable Orifice Valve 310 to control flow and insure "delivered" volume equals "set" volume.

The Autocal Valve 320 is used to set the zero pressure baseline during the startup Self-Check and at regular intervals during operation. The Autocal Valve 320 works in conjunction with the Disposable Ventilator Circuit's 400 Pressure Line 410, the Proximal Pressure Transducer 140 and the CPU 200. The signal output of the Proximal Pressure Sensor 140 represents any offset that may exist between the input open to atmospheric pressure and pressure line input from the Ventilator Circuit 400 through the Autocal Valve 320. Solenoid #1 of the Exhalation Valve Manifold 330 is used to control a Disposable Ventilator Circuit's 400 Exhalation Valve Control Line 430. When de-energized, Solenoid #1 keeps the Exhalation Valve Control Line 430 open to atmosphere. When energized, it causes an Exhalation Valve 451 diaphragm to close, forcing delivered gas into the patient inspiration or the partial retention of delivered volume during exhalation (PEEP).

Solenoid #2 of the Exhalation Valve Manifold 340 is used as a safety backup for Solenoid #1. Solenoid #2 is normally closed in its de-energized state, which allows Solenoid #1 to have complete control over the Exhalation Valve Diaphragm 451. Solenoid #2 is energized when a failure of Solenoid #1 is detected and results in the Exhalation Valve Control Line 430 being opened to atmosphere.

Ventilator Circuit

The Disposable Ventilator Circuit 400 interfaces between the patient and the ventilator via connecting tubing. The ventilator controls its Exhalation Valve 450, 451 and 452 to allow breathing gas to pass to and from the patient during inspiration and exhalation. The Pressure Line 410 connects the Disposable Ventilator Circuit's 400 most distal connector to the Differential Pressure Transducer 150. The Pressure Line 410 signal (valve) is used to measure and display airway pressure and is part of the delivered/exhaled volume pneumotach. The Pressure Line 410 together with the Delivered Flow/Exhaled Flow Line 420 provide the pressure signals used to measure the pressure drop across the pneumotachs fine mesh screen 460, The Delivered Flow/Exhaled Flow Line 420 connects the ventilator-side of the delivered/exhaled volume pneumotach to the Differential Pressure Transducer 150. The Delivered Flow/Exhaled Flow Line 420 along with the Pressure Line 410 provide the pressure signals used to measure the pressure drop across the pneumotachs fine mesh screen 460. The Exhalation Valve Control Line 430 connects the ventilator's Exhalation Valve Manifold 330 and 340 pneumatic control signal to the Exhalation Valve Diaphragm 451 via the Exhalation Valve Cap 450.

The Inspiratory Line 440 connects the ventilator's "Gas To Patient" connector with the Disposable Ventilator Circuit's 400 exhalation valve input. During inspiratory periods, gas is allowed to flow through the Inspiratory Line 440, Exhalation Valve 450-453, Delivered Flow/Exhaled Flow Mesh Screen 460, HME 470 and Patient Connection 480 to the patient. The Inspiratory Line 440 isolated from with expiratory gas flow.

The Exhalation Valve Cap 450 secures the Exhalation Valve Diaphragm 451 to the Exhalation Valve Body 452 and includes a hose fitting that attaches to one end of the Exhalation Valve Control Line 430. The Exhalation Valve Diaphragm 451 is normally de-energized when gas is not flowing, which allows gas to pass unrestricted from the patient into the atmosphere. The Exhalation Valve Diaphragm 451 is energized closed during inspiratory cycles thereby forcing delivered gas into the patient and when retention of a part of the delivered volume is saved during exhalation (PEEP). Pneumatic control signals are applied through the Exhalation Valve Control Line 430 and Exhalation Valve Cap 450 to the Exhalation Valve Diaphragm 451. The Exhalation Valve Body 452 houses the Exhalation Valve Diaphragm 451 and connects with the Exhalation Valve Cap 450, the Condensate Diverter Elbow 453 and a Ventilator Circuit Tee 461. The Exhalation Valve Body 452 also contains a hose fitting that attaches to one end of the Delivered Flow/Exhaled Flow Line 420.

A Condensate Diverter Elbow 453 attaches to the Exhalation Valve Body 452. This component functions as a small trap for exhaled condensate when the exhalation valve assembly is oriented vertically. The Delivered Flow/Exhaled Flow Mesh Screen 460 is located between the Exhalation Valve Body 452 hose fitting that attaches to one end of the Delivered Flow/Exhaled Flow Line 420 and the Ventilator Circuit Tee 461 hose fitting connected to one end of the Pressure Line 410. The mesh screen 460 provides a slight resistance to the flow of gas during inspirations and exhalations. This resistance is sensed as a small pressure drop and is quantified (measured) by the Differential Pressure Transducer 150. The pressure drop is then compared to data contained within the ventilator's memory ("look-up table"). The look-up table data contains a gas flow value (calibrated for oxygen) equivalent to each measured pressure drop over the ventilator's usable range. The Ventilator Circuit Tee 461 connects to the patient-side of the Exhalation Valve and the HME 470. It contains a hose fitting connected to one end of the Pressure Line 410. The HME 470 (i) provides self-humidification by recycling moisture from the patient's previous exhalation back to the patient and (ii) protects the Delivered Flow/Exhaled Flow Mesh Screen 460 from collecting condensate. Such condensate would distort pressure drop readings by causing a higher reading than actual. The Patient Connection 480 is a standard 22 mm/15 mm OD/ID fitting that interfaces with masks, endotracheal tubes, or tracheostomy tubes.

Mechanicals

Further mechanical elements include Air Filter 500 that traps particulate which would otherwise enter the Internal Compressor 510 and be passed along to the patient and Delivered Flow/Exhaled Flow Mesh Screen 460. As with condensate, particulate could collect in the screen and distort pressure drop readings, i.e., higher than actual. The Internal Compressor 510 allows the ventilator to function independent of an external gas source. When cycled "On", the Internal Compressor 510 provides filtered air to the patient, or filtered air that can be mixed with external oxygen, for delivery to the patient, through the Air/Oxygen Mixer 520 and Disposable Ventilator Circuit 400. The Air/Oxygen Mixer 520 is a manifold for passing gas or mixing gases intended for delivery to the patient. Ventilator 10 can be manufactured to deliver 100% Oxygen only (Model A) or operate in a variety of selectable delivery modes (Model B), preferably such as:

Model A—100% Oxygen

Model B—
 External Air
 External Air+External Oxygen (adjustable, 21 to 100%)
 Internal Air
 Internal Air+External Oxygen (adjustable, 21 to 100%)

The following components are mechanically attached to, or physically contained within, the Air/Oxygen Mixer 520. The function of each component is described above:

External Air Input Pressure Sensor 100
External Oxygen Input Pressure Sensor 110
External Air Flow Sensor 120
External Oxygen Flow Sensor 130
Proximal Pressure Sensor 140
External Air Variable Orifice Valve 300
External Oxygen Variable Orifice Valve 310
Autocal Valve 320
Solenoid #1 of the Exhalation Valve Manifold 330
Solenoid #2 of the Exhalation Valve Manifold 340
Internal Compressor 510

In exemplary Model A, oxygen passes through the Air/Oxygen Mixer 520 to the Disposable Ventilator Circuit's 400 Inspiratory Line 440 and Solenoid #1 of the Exhalation Valve Manifold 330. Model A has no gas mixing capability.

In exemplary Model B, oxygen, external air or air from the Internal Compressor 510 passes through the Air/Oxygen Mixer 520 to the Disposable Ventilator Circuit's 400 Inspiratory Line 440 and Solenoid #1 of the Exhalation Valve Manifold 330.

If the Air/Oxygen mixture set point is 21% or 100%, no gas mixing takes place and the air or oxygen simply passes through the mixer.

If the Air/Oxygen mixture set point is set between 22% and 99%, the microprocessor 200 apportions how much air and how much oxygen is required to meet the "set" oxygen mixture (percentage) and "set" volume requirements.

Operator Controls

Exemplary operator interface switches and controls will now be described. Pressing a Power Pushbutton Switch 600 applies or removes operating power. The Rotary Encoder Pushbutton Switch 610 allows the operator to make and enter operating mode and function settings described below. The Alarm Mute/Cancel function is part of the Rotary Encoder Pushbutton Switch 610. This function allows the operator to mute or cancel specific alarms. The Manual Breath Pushbutton Switch 620 permits delivery of one ventilator-generated breath. The manual breath is equal in duration and volume to the current inspiratory time and "set" volume settings.

Estimated Patient Weight Settings

According to the principles of the present invention, ventilator 10 enables the operator to enter and store data representing a patient's individual weight. CPU applies such data to stored algorithm to generate control signals to vary the durations, phases, and volumes of tidal air delivery and exhalation.

The operator enters the patient's estimated weight by using rotary switch 610 to bring the weight menu to the display, turning knob 610 to the estimated weight and pressing knob 610 to enter the weight data into storage.

Default weight related values of Rate, I, VT, MVV, and Pressure Relief/Alarm Setpoint are also separately stored for use in various procedures such as those described below. Preferably, Radford Default Values, such as those shown in FIGS. 5 and 6, are stored for adult and child patient ventilation.

Exemplary Ventilator Package Design

With reference to Figure X, one preferred embodiment of portable ventilator 10 can have an internal frame that supports one or more printer circuit boards to which electrical and device elements are mounted (all not shown). Ventilator 10 also includes a universal AC power supply/docking module (not shown). Housing 20 includes two opposite and removable side panels 22 that fasten to the internal frame, an input-output (JO) panel 24 and a control panel 26. Alpha-numeric display 28 and indicator lights 30 mount on panel 26 along with controls "store/save-set value" push button switch/rotary encoder knob 610, "manual [breath] push button switch" 620, and IO power switch 600.

Ventilator 10 includes gas outlet hose connector 38 mounted to but connected through panel 24. A conventional anti-asphyxia leave valve (not shown) internally mounts in communication with connector 38. Oxygen inlet fitting 40 also mounts to panel 24. Flow transducer hose barbs 42, 44 and exhalation valve hose barb 46 are also provided. Elements 38, 40, 42, 44 and 46 can connect to a disposable ventilator pneumatic circuit better seen in FIG. 2 at 400. One example of the controls for circuit 400 elements is shown in Figure Y.

The rotary encoder pushbutton switch knob 610 enables the operator to perform various functions hereafter, all references to "SET VALUE" and "SELECT" shall pertain to the rotary encoder, and all references to "STORE", "SAVE" and "ENTER" shall pertain to its integral pushbutton switch.

The Rotary Encoder with Integral Pushbutton Switch is used to: Make selections—Turning its rotary component clockwise or counterclockwise moves the highlight cursor ("reverse video") from one selection to another.

Set values—Turning knob 610 rotary component clockwise or counterclockwise changes the value of a selection up or down (increase or decrease).

Store (ENTER) the selection or value by pressing knob 610 momentary pushbutton switch.

Save (ENTER) the selection or value by pressing knob 610 momentary pushbutton switch.

Using the Rotary Encoder with Integral Pushbutton Switch 610 the operator can: SELECT, STORE and SAVE the patient's approximate individual characteristic such as estimated weight.

Change the existing weight setting.

Change the default high-pressure alarm/peak inspiratory pressure relief setting.

Enable PEEP "ON" or set PEEP back to its "OFF" (default) setting.

Mute an Operating Alarm or Cancel an Advisory Alarm.

Pressing the manual breath switch 620 during operation initiates delivery of one MANUAL BREATH. Each MANUAL BREATH is equal to one complete ventilatory cycle, in the selected Operating Mode (except as noted below). Such cycle includes the current INSPIRATORY TIME/TIDAL VOLUME "settings" and expiratory time period.

If selected Operating Mode is CPR MASK with adult values (a weight setting 25 Kg or greater), pressing the MANUAL BREATH Pushbutton 620 will generate, e.g., a 2-second inspiration and 4-second exhalation (1:2 I:E Ratio). If desired, ventilator 10 can be made to support a manual "second breath" with, e.g., 1:4 I:E Ratio.

A MANUAL BREATH should not be delivered until airway pressure sensor indicates the pressure has reached the expiratory baseline (zero or PEEP). Each time a MANUAL BREATH is triggered by pressing switch 610, an audible "beep" is generated to advise the operator. The MANUAL BREATH Pushbutton should be protected against accidental contact by a cylindrical guard, generally as shown.

For a patient with no spontaneous breath in whom the patient or operator wants to maintain a constant I:E of 1:3 with no stacked breaths, the microprocessor can be programmed to store the following exemplary algorithm to set the Inspiratory flow (liters/min): $VI_{SPON}=3(V_T/V_{ESPON})$.

Ventilator 10 operation and methods will now be described.

OPERATION (Note: # paragraphs are not continuous and references to letters are to the letters circled in the respective drawing Figures herein. "?" means an operator choice or change of manual settings (e.g., parameter) or choice of mode selection.

2. Set Power to "On": the POWER pushbutton switch allows the operator to power the ventilator from "OFF" to "ON". To power "ON", depress the switch for 1 second.

4. Set Operating Mode: the operator selects 1 of 4 operating modes: CRP Mask Mode, CPR Tube Mode, Quick-Start Mask Mode, or Quick-Start Tube Mode (described below).

6. Set Patient Weight: the operator is required to enter an estimate of the patient's ideal: body weight. To enter the weight, the operator turns the rotary encoder which increments the weight values up or down. Weights are displayed simultaneously in both pounds (lbs) and kilograms (kg).

8. Confirm Setting: after each operator-initiated action, the operator is asked to confirm the resultant change. The user is given the option of accepting ("YES"), returning to modify the action ("NO") or exiting the Change Settings Menu ("EXIT").

9. Begin Operation: once the user has confirmed the selected settings the ventilator immediately begins operation.

Ventilation Mode Selection

10. Set Quick-Start Mask Mode: in the QUICK-START MASK Operating Mode, the $V_T$ Alarm (Tidal Volume), comparing exhaled volume to delivered volume and delivered volume to set volume, is an Advisory Alarm. It triggers when exhaled volume is more than 25% less than delivered volume or delivered volume is more than 20% less than set volume. When initiated, the $V_T$ alarm is accompanied by a message in the LCD's AMC that includes the actual percentage offset. This alarm can be easily influenced by mask leakage. Once the Alarm Mute/Cancel Pushbutton Switch is pressed, the audible component of this alarm is disabled until power is recycled to "OFF" and then "ON" again. The accompanying Alarm LED illuminates as applies, as does its AMC message. This alarm along with the accompanying message guide the operator to assure a secure seal while ventilating patients with a mask.

12. Set Weight: the operator is required to enter an estimate of the patient's ideal body weight. To enter the weight, the operator turns the rotary encoder which increments the weight values up or down. Weights are displayed simultaneously in both pounds (lbs) and kilograms (kg).

14. Tube?: in selecting the operating mode the user is required to determine wither the patient has a protected or unprotected airway. An unprotected airway requires that the operator ventilate the patient using a securely fitting oral/nasal mask. Protected airways include a device that is used to assure a patient airway suitable for positive pressure ventilation. A number of methods are available to secure the airway: endotracheal tube, Combitube, intubating laryngeal mask airway, tracheostomy, cricothyrotomy, etc.[1] [2]

16. Set Quick-Start Tube Mode: in the QUICK-START TUBE Operating Mode, the $V_T$ Alarm (Tidal Volume), comparing exhaled volume to delivered volume and delivered volume to set volume, is an Operating Alarm. It triggers when exhaled volume is more than 20% less than delivered volume or delivered volume is more than 20% less than set volume. When initiated, the $V_T$ alarm is accompanied by a message in the LCD's AMC that includes the actual percentage offset. This alarm is less likely to be influenced by leakage. Once the Alarm Mute/Cancel Pushbutton Switch is pressed, the audible component of this alarm is muted for 30 seconds. The accompanying Alarm LED illuminates as applies, as does its AMC message.

18. CPR?: CPR Operating Modes are designed in accordance with published International ECC and CPR Guidelines 2000. Each Mode simplifies and insures qualitative CPR delivery by carefully maintaining precise performance in conjunction with safety features to protect the patient and operator against harm during use.

20. Tube?: see #14.

22. Set CPR Tube Mode: in the CPR TUBE Operating Mode, controlled ventilations are delivered to the patient's protected airway. Controlled ventilations are mandatory ventilations delivered at fixed intervals. They are triggered irrespective of the presence of spontaneous breathing. Ventilator-generated breaths are delivered in accordance with published International ECC and CPR Guidelines 2000 for Rate, Inspiration Time, Inspiratory/Expiratory Ratio (I:E) and Gas Flow/Kilogram. Volume is determined by patient weight (operator-selected).

In accordance with published International ECC and CPR Guidelines 2000, the following defaults apply:
Rate:
Adults: 10 ventilations per minute
Children: 20 ventilations per minute
Inspiration Time:
Adults: 2.0-seconds
Children: 1.0-seconds
I:E Ratio:
Adults: 1:2
Children: 1:2
Gas Flow:
Adults: 30 Liters Per Minute
Children: 15 Liters Per Minute
Delivered Volume:
Adults: 1000 ml (unless pressure limit setpoint is exceeded)
Children: 500 ml (unless pressure limit setpoint is exceeded)

Pressure Limiting: 60 cmH$_2$O (default value), adjustable range is 20 to 80 cmH$_2$O The ventilator determines whether the patient is an adult or child when the operator enters the patient's approximate weight. Accordingly, the International ECC and CPR Guidelines 2000 default values for adult or child are invoked. The operator may change the patient's approximate weight setting at any time before or during operation. To reduce "dead space" and "compressible volume", the Model, ventilator's pediatric ventilator circuit should always be used whenever pediatric operation is selected.

The ventilator LCD screen continuously displays settings, directions, airway-pressure information and battery status during operation.

In the CPR TUBE Operating Mode, the V$_T$ Alarm (Tidal Volume), comparing exhaled volume to delivered volume and delivered volume to set volume, is an Operating Alarm. It triggers when exhaled volume is more than 10% less than delivered volume or delivered volume is more than 10% less than set volume. When initiated, the V$_T$ alarm is accompanied by a message in the LCD's AMC that includes the actual percentage offset. This alarm is less likely to be influenced by leakage. Once the Alarm Mute/Cancel Pushbutton Switch is pressed, the audible component of this alarm is muted for 30 seconds. The accompanying Alarm LED illuminates as applies, as does its AMC message.

The CPR TUBE Operating Mode includes a metronome to guide rescuers in their performance of CPR. The metronome produces an audible "chirp" accompanied by an illuminating LED whenever chest compression is required. Because this device is intended for use by emergency personnel, it assumes that 2 rescuers are performing CPR (but applies equally if there is only 1 rescuer), and its metronome is timed in accordance with published International ECC and CPR Guidelines 2000 for use on intubated patients.

The following metronome defaults apply:

| CPR WITHOUT MASK | ADULT | CHILD |
| --- | --- | --- |
| Compression/Ventilation Ratio | 5:1 | 5:1 |
| Inspiration Time | 2 seconds | 1 second |
| Time sequence per cycle (seconds) | 2, 4 | 1, 2 |
| Number of cycles per minute | 10 | 20 |

24. Set CPR Mask Mode: in the CPR MASK Operating Mode, controlled ventilations are delivered via the operator-held mask to the patient's unprotected airway. Controlled ventilations are mandatory ventilations delivered at fixed intervals. They are triggered irrespective of the presence of spontaneous breathing. Ventilator-generated breaths are delivered in accordance with published, for example, International ECC and CPR Guidelines 2000 for Rate, Inspiration Time, Inspiratory/Expiratory Ratio (I.E) and Gas Flow/Kilogram. Volume is determined by patient weight (operator-selected).

In accordance with published International ECC and CPR Guidelines 2000, the following defaults apply:
Rate:
Adults: 8 ventilations per minute
Children: 20 ventilations per minute
Inspiration Time:
Adults: 2.0-seconds
Children: 1.0-seconds
I:E Ratio:
Adults: Cyclic—1:1, 1:4.5 then repeats
Children: 1:2
Gas Volume:
Adults: 7 ml/Kg
Children: 7 ml/Kg
Pressure Limiting: 30 cmH$_2$O (default value), adjustable range is 20 to 80 cmH$_2$0

The Model Ventilator™ determines whether the patient is an adult or child when the operator enters the patient's approximate weight. Accordingly, the International ECC and CPR Guidelines 2000 default values for adult or child are invoked. The operator may change the patient's approximate weight setting at any time before or during operation. To reduce "dead space" and "compressible volume", the Model ventilator's pediatric ventilator circuit should always be used whenever pediatric operation is selected.

The ventilator LCD screen continuously displays current and updated settings, directions, airway-pressure information and battery status during operation.

In the CPR MASK Operating Mode, the V$_T$ Alarm (Tidal Volume), comparing exhaled volume to delivered volume and delivered volume to set volume, is an Advisory Alarm. It triggers when exhaled volume is more than 25% less than delivered volume or delivered volume is more than 25% less than set volume. When initiated, the V$_T$ alarm is accompanied by a message in the LCD's AMC that includes the actual percentage offset. This alarm can be easily influenced by mask leakage. Once the Alarm Mute/Cancel Pushbutton Switch is pressed, the audible component of this alarm is disabled until power is recycled to "OFF" and then "ON" again. The accompanying Alarm LED illuminates as applies, as does its AMC message.

Quick-Start Mask Mode

26. SET DEFAULT SETTINGS FROM TABLE: See #24
27. FIGS. 8, 9 REFERENCE B: reference from the VENTILATION MODE SELECTION flow diagram.
28. HIGH PEAK PRESSURE?: during first 4 breaths the High Peak Pressure auditory alarm is disabled. During this time, the Model Ventilator™ assess the peak inspiratory pressure. If the peak inspiratory pressure of the first delivered breath is greater than the Pressure Relief Alarm Setpoint (see Appendix 1), then the respiratory rate is increased by 10% and the tidal volume is decreased by 10%. Using this approach, the default minute volume is maintained will the ventilator attempts to decrease the peak inspiratory pressure. If the peak inspiratory pressure second breath is greater than the Pressure Relief Alarm Setpoint, then the respiratory rate is increased by 10% (20% total) and the tidal volume is decreased by 10% (20% total). If the peak inspiratory pressure remains greater than the Pressure Relief Alarm Setpoint, then the auditory High Pressure Alarm is enabled and High Pressure Alarm message is displayed on the LCD screen. The user is also prompted that the patient's weight may be too high, the patient's airway may be occluded or that the ventilator tubing may be kinked.

The patient is protected from high airway pressure during all ventilations by a pressure relief mechanism based on the patient's weight (see Appendix 1). The High Pressure Relief has a range from 20 to 80 cm H$_2$O that the operator may change independent of the patient's weight setting, at any time during operation.

30. INCREASE RR MAINTAIN VMIN: if the Peak Inspiratory Pressure is greater than the Default Pressure Relief Setpoint, the Model Ventilator™ increases the respiratory rate by 10% and decreases the tidal volume by 10% maintaining minute volume and reducing the peak inspiratory pressure, see #28 for a complete description.

32. HIGH PEAK PRESSURE?: the patient is protected from high airway pressure during all breaths by a pressure relief mechanism based on the patient's weight (see Appendix 1). The High Pressure Relief has a range from 20 to 80 cm $H_2O$ that the operator may change independent of the patient's weight setting, at any time during operation.

34. INCREASE RR MAINTAIN VMIN: if the Peak Inspiratory Pressure is greater than the Default Pressure Relief Setpoint, the Model Ventilator™ increases the respiratory rate by 10% and decreases the tidal volume by 10% maintaining minute volume and reducing the peak inspiratory pressure, see #28 for a complete description.

36. HIGH PEAK PRESSURE?: see #32 for description.

38. CHANGE SETTINGS?: during operation, if it becomes necessary to change a setting (ventilation mode, new patient weight, pressure limit Setpoint, or positive end-expiratory pressure), the user pushes the encoder 2 times to open the CHANGE SETTINGS Menu Screen. (See CHANGE SETTING, QS MODES, #138-174, and CHANGE SETTING, CPR MODES #180-218 for detailed description.)

40. FIG. 9 REFERENCE I: this is the reentry point following a change in the Pressure Relief/Alarm Setpoint on the CHANGE SETTINGS, QS MODE flow diagram.

41. FIG. 9 REFERENCE F: references to the CHANGE SETTINGS, QS MODE flow diagram.

42. POWER OFF?: at any time during operation the user can select to turn the unit off. To do this, the user presses and holds the Power Switch for 3 seconds. A screen prompt then asks the user to confirm power off. The default selection is yes and the user is only required to press the encoder once to turn the unit off. If the user selects no, the screen reverts back to the operating screen.

When the Model Ventilator™ is connected to external power during power off, the unit does not turn completely off. A Power Management screen is displayed indicating the charging status of the internal battery.

44. END OPERATION: indicates the ventilator is no longer in operation. See #42 for additional information.

Quick-Start Tube Mode

46. Set Default Settings From Table: see #24.

47. FIG. 10 REFERENCE C: reference from the VENTILATION MODE SELECTION flow diagram.

48. HIGH PEAK PRESSURE?: see #28 for description.

50. INCREASE RR MAINTAIN VMIN: see #30 for description.

52. HIGH PEAK PRESSURE?: see #32 for description.

54. INCREASE RR MAINTAIN VMIN: see #34 for description.

56. HIGH PEAK PRESSURE?: see #36 for description.

58. FIG. 10 REFERENCE J: this is the reentry point after a new Pressure Relief/Setpoint value has been entered in the CHANGE SETTING, QS MODE flow diagram.

60. CHANGE SETTINGS?: see #38 for description.

61. FIG. 10 REFERENCE F: reference to the CHANGE SETTINGS, QS MODE flow diagram.

62. POWER OFF?: see #42 for description.

CPR Tube Mode

See #22 for a complete description of CPR TUBE mode.

64. WEIGHT>24 KG?: patients greater than 24 kg are treated using the adult default settings following the International ECC and AHA CPR Guidelines 2000 CPR procedures. NOTE: To reduce breathing dead space and compressible volume, the Model ventilator's pediatric ventilator circuit should always be used whenever pediatric operation is selected.[3]

65. FIGS. 8, 11 REFERENCE D: reference from the VENTILATION MODE SELECTION flow diagram.

66. SET I-TIME=2.0 SEC: International ECC and AHA CPR Guidelines 2000 procedures call for the use of a 2.0 second inspiratory time when ventilating an adult with a protected airway.[3]

68. SET I:E=1:2: International ECC and AHA CPR Guidelines 2000 procedures call for the use of a 1:2 I:E ratio when ventilating an adult with a protected airway.[3]

70. SET VT=1000 ML: International ECC and AHA CPR Guidelines 2000 procedures call for the use of a 1000 ml tidal volume when ventilating an adult with a protected airway.[3]

72. CONFIRM SETTINGS: see #8 for description.

74. FIG. 11 REFERENCE L: this is the reentry point after a new High Pressure Limit has been entered on the CHANGE SETTING, CPR MODES flow diagram.

76. BEGIN OPERATION: see #9 for description.

78. 5 COMPRESSIONS @ 100/MIN: International ECC and AHA CPR Guidelines 2000 CPR procedures call for a chest compression rate of 100 compressions/minute when performing CPR.[3]

80. 1 BREATH: International ECC and AHA CPR Guidelines 2000 CPR procedures call for 1 breath for every 5 chest compression when performing CPR on an adult with a protected airway.[3]

82. CHANGE SETTINGS: see #28 for description.

84. SET I-TIME=1.0 SEC: International ECC and AHA CPR Guidelines 2000 procedures call for the use of a 1.0 second inspiratory time when ventilating a child with a protected airway.[3]

86. SET I:E=1:2: International ECC and AHA CPR Guidelines 2000 procedures call for the use of a 1:2 I:E ratio when ventilating a child with a protected airway.[3]

88. SET VT=500 ML: International ECC and AHA CPR Guidelines 2000 procedures call for the use of a 500 ml tidal volume when ventilating a child with a protected airway.[3]

90. CONFIRM SETTINGS: see #8 for description.

92. FIG. 11 REFERENCE M: this is the reentry point after a new High Pressure Limit has been entered on the CHANGE SETTING, CPR MODES flow diagram.

94. 5 COMPRESSIONS @ 100/MIN: International ECC and AHA CPR Guidelines 2000 CPR procedures call for a chest compression rate of 100 compressions/minute when performing CPR.[3]

96. 1 BREATH: International ECC and AHA CPR Guidelines 2000 CPR procedures call for 1 breath for every 5 chest compression when performing adult CPR on a patient with a protected airway.[3]

98. CHANGE SETTINGS?: see #38 for description.

CPR Mask Mode

See #22 for a complete description of CPR MASK mode.

100. WEIGHT>24?: patients greater than 24 kg are treated using the adult default settings following the International ECC and AHA CPR Guidelines 2000 CPR procedures. NOTE: To reduce breathing dead space and compressible volume, the Model ventilator's pediatric ventilator circuit should always be used whenever pediatric operation is selected.[3]

101. FIG. 12 REFERENCE E: reference from the VENTILATION MODE SELECTION flow diagram.

102. SET I-TIME=2.0 SEC: International ECC and AHA CPR Guidelines 2000 procedures call for the use of a 2.0 second inspiratory time when ventilating an adult using a facemask.[3]

104. SET I:E=1:2: International ECC and AHA CPR Guidelines 2000 procedures call for the use of a 1:2 I:E ratio when ventilating an adult with a facemask.[3]

106. SET TIDAL VOLUME=7 ML/KG: International ECC and AHA CPR Guidelines 2000 procedures call for the use of a 6-7 ml/kg tidal volume when ventilating a patient without a protected airway.[3]

108. CONFIRM SETTINGS: see #8 for description.

110. FIG. 12 REFERENCE N: this is the reentry point after a new High Pressure Limit has been entered on the CHANGE SETTING, CPR MODES flow diagram.

112. BEGIN OPERATION: see #9 for description.

114. 15 COMPRESSIONS @ 100/MIN: International ECC and AHA CPR Guidelines 2000 CPR procedures call for a 5:1 chest compression to breath ratio when performing CPR on an adult without a protected airway.[3]

116. 2 BREATHS: International ECC and AHA CPR Guidelines 2000 CPR procedures call for 2 breaths for every 15 chest compression when performing CPR on an adult without a protected airway.[3]

118. CHANGE SETTINGS: see #28 for description.

120. SET I-TIME=1.0 SEC: International ECC and AHA CPR Guidelines 2000 procedures call for the use of a 1.0 second inspiratory time when ventilating a child without a protected airway.[3]

122. SET I:E=1:2: International ECC and AHA CPR Guidelines 2000 procedures call for the use of a 1:2 I:E ratio when ventilating a child without a protected airway.[3]

124. SET TIDAL VOLUME=7 ML/KG: 7 ML/KG: International ECC and AHA CPR Guidelines 2000 procedures call for the use of a 6-7 ml/kg tidal volume when ventilating a patient without a protected airway.[3]

126. CONFIRM SETTINGS: see #8 for description.

128. FIG. 12 REFERENCE 0: this is the reentry point after a new High Pressure Limit has been entered on the CHANGE SETTING, CPR MODES flow diagram.

130. BEGIN OPERATION: see #9 for details.

132. 5 COMPRESSIONS @ 100/MIN: International ECC and AHA CPR Guidelines 2000 CPR procedures call for a 5:1 chest compression to breath ratio when performing CPR on a child without a protected airway.[3]

134. 1 BREATH: International ECC and AHA CPR Guidelines 2000 CPR procedures call for 1 breath for every 5 chest compression when performing CPR on a child without a protected airway.[3]

136. CHANGE SETTINGS: see #38 for description.

Change Settings, QS Mode

During operation if it becomes necessary to change a setting, this can be accomplished by pressing the encoder 2 times. This opens the CHANGE SETTINGS MENU SCREEN, which allows the user to select a new mode of operation, set a new patient weight, set a new high-pressure limit, or add or remove PEEP. If the CHANGE SETTINGS MENU SCREEN was opened inadvertently, the user may also return to the previous operating screen by selecting CONTINUE CURRENT SETTINGS.

138. SET NEW MODE?: SET NEW MODE is the default selection. By pushing the rotary encoder, the MODE selection menu is opened and the current operating mode is highlighted. Using the encoder, the user can select any of the operating modes by turning the encoder to highlight the desired mode and pressing the encoder. Note: the user may select the current operating mode. Doing this, allows the user to enter a new patient weight and resets the high-pressure limit to the default value.

140. FIG. 13 REFERENCE G: reference to CHANGE SETTINGS/RETURN TO MODE flow diagram.

142. SET NEW WEIGHT?: by highlighting SET NEW WEIGHT and pressing the encoder, the user is able to enter a new patient weight. See #6 for additional details.

144. FIG. 8 REFERENCES B: reference to QUICK-START MASK MODE flow diagram.

146. TUBE?: see #14 for description.

148. ON-PAGE REFERENCE C: reference to QUICK-START TUBE MODE flow reference.

150. SET HIGH PRESSURE LIMIT?: by highlighting the SET HIGH PRESSURE LIMIT and pressing the encoder, the current high-pressure alarm/limit is displayed. Turning the encoder increases or decreases the value. Pressing the encoder stores the value. NOTE: the range of the HIGH PRESSURE alarm/limit is 10-80 cm $H_2O$.

152. ENTER NEW VALUE: the user is prompted to enter a new value.

158 CONFIRM SETTINGS: see #8 for description.

160. ON-PAGE REFERENCE H: reference to insert figure #158 on the CHANGE SETTINGS, QS MODE flow diagram.

162. SET PEEP?: by highlighting the SET PEEP and pressing the encoder, the user can add 5 cm $H_2O$ of positive end-expiratory pressure (PEEP). The Model ventilator only allows zero baseline pressure or 5 cm 1120. NOTE: the default start-up PEEP is zero cm $H_2O$.

164. CONTINUE CURRENT SETTINGS: allows the user to exit the CHANGE SETTINGS window without effecting the current mode or settings.

168. CONFIRM SETTINGS: see #8 for description.

170. FIG. 13 REFERENCE H: see #160 for details.

176. FIG. 13 REFERENCE I: the reentry point in the QUICK-START MASK MODE flow diagram.

177.

178. FIG. 13 REFERENCE J: the reentry point in the QUICK-START TUBE MODE flow diagram.

Change Settings, CPR Modes

During operation, if it becomes necessary to change a setting, this can be accomplished by pressing the encoder 2 times. This opens the CHANGE SETTINGS MENU SCREEN, which allows the user to select a new mode of operation, set a new patient weight, or a new high-pressure limit. If the CHANGE SETTINGS MENU SCREEN was opened inadvertently, the user may also return to the previous operating screen by selecting CONTINUE CURRENT SETTINGS.

180. SET NEW MODE?: see #138 for description.

182. FIG. 13 REFERENCE G: reference to the CHANGE SETTINGS/RETURN TO MODE flow diagram.

184. SET NEW WEIGHT?: see #142 for description.

186. ENTER NEW VALUE: see #152 for description.

187. CONFIRM SETTINGS: see #8 for description.

188. TUBE?: see #14 for description.

190. FIG. 12 REFERENCE E: reference to CPR MASK MODE flow diagram.

192. FIG. 11 REFERENCE D: reference to CPR TUBE MODE flow diagram.

194. SET HIGH PRESSURE LIMIT?: see #150 for description.

196. CONTINUE CURRENT SETTINGS: see #164 for description.

198. ENTER NEW VALUE: see #152 for description.

204. CONFIRM SETTINGS: see #8 for description.

206. TUBE?: see #14 for description.

208. WEIGHT>24 KG: see #64 for description.

210. FIG. 14 REFERENCE O: reference to reentry point on CPR MASK MODE flow diagram.

212. FIG. 14 REFERENCE N: reference to reentry point in CPR MASK MODE flow diagram.

214. WEIGHT>24 KG: see #64 for description.

216. FIG. 14 REFERENCE L: reference to reentry point on CPR TUBE MODE flow diagram.

218. FIG. 8 REFERENCE M: reference to reentry point on CPR TUBE MODE flow diagram.

Change Settings/Return to Mode

220. CPR?: see #18 for description.

222. TUBE?: see #14 for description.

224. FIG. 9 REFERENCE E: reference to CPR MASK MODE flow diagram.

226. FIG. 14 REFERENCE D: reference to CPR TUBE MODE flow diagram.

228. TUBE?: see #14 for description.

230. FIGS. 8, 10 REFERENCE C: reference to QUICK-START TUBE MODE flow diagram.

232. FIGS. 8, 9 REFERENCE B: reference to QUICK-START MASK MODE flow diagram.

Other improvements and changes can be made to the herein disclosed exemplary embodiment without departing from the spirit and scope of the present invention.

REFERENCE LIST

1. Foley L J, Ochroch E A. Bridges to establish an emergency airway and alternate intubating techniques. Crit Car Clin 2000; 16:429-44, vi.
2. Anonymous. Guidelines 2000 for Cardiopulmonary Resuscitation and Emergency Cardiovascular Care. Part 6: advanced cardiovascular life support: section 3: adjuncts for oxygenation, ventilation and airway control. The American Heart Association in collaboration with the International Liaison Committee on Resuscitation. Circulation 2000; 102:195-104.
3. Pepe P E, Gay M, Cobb L A, Handley A J, Zaritsky A, Hallstrom A, et al. Action sequence for layperson cardiopulmonary resuscitation. Ann Emerg Med 2001; 37:S17-25.

The invention claimed is:

1. A ventilator apparatus, comprising:
a portable housing;
a pneumatic assembly disposed in the portable housing, the pneumatic assembly being configured to output gas to be delivered to a patient's airway; and
a controller disposed in the portable housing and in communication with the pneumatic assembly, the controller being configured to operate the pneumatic assembly to output gas to the patient's airway,
wherein the controller is configured to operate the pneumatic assembly to output gas to the patient's airway at fixed intervals and according to two or more breath delivery parameters, the two or more breath delivery parameters comprising a ventilation rate and a tidal volume,
wherein the controller is further configured to generate a periodic synchronization signal for a chest compression to be performed on the patient when administering CPR to the patient and to sequence, in a manner suitable for administering CPR to the patient, the generation of periodic synchronization signals with the operation of the pneumatic assembly to output gas to the patient's airway at the fixed intervals,
wherein the controller is configured to receive an input of a patient size characteristic and to determine an initial tidal volume based on the patient size characteristic input to the controller,
wherein the controller is configured to assess a peak inspiratory pressure of the gas output to the patient's airway and adjust the ventilation rate and the tidal volume to reduce the peak inspiratory pressure and maintain a desired minute volume of the gas output to the patient's airway when the assessed peak inspiratory pressure exceeds a predetermined threshold pressure,
wherein the controller is configured to determine the two or more breath delivery parameters in accordance with one or more CPR operational modes input to the controller, the one or more CPR operational modes comprising at least a CPR tube mode and a CPR mask mode,
wherein the controller is configured to receive a selection between the CPR tube mode and the CPR mask mode,
wherein the CPR tube mode is selected when the patient's airway requires the use of a tube device for ventilation and the CPR mask mode is selected when the patient's airway requires the use of a mask for ventilation, and
wherein the controller is configured to determine different two or more breath delivery parameters when the CPR tube mode is input to the controller than when the CPR mask mode is input to the controller.

2. The ventilator apparatus according to claim 1, further comprising at least one operator control disposed on the portable housing, the at least one operator control comprising a patient parameter input control configured to be manipulated to input at least one patient parameter to the controller,
wherein the at least one patient parameter input to the controller comprises the patient size characteristic.

3. The ventilator apparatus according to claim 2, wherein the patient size characteristic input to the controller comprises an estimated patient weight.

4. The ventilator apparatus according to claim 3, wherein the controller is configured to determine if the patient is a child or adult based on the estimated patient weight.

5. The ventilator apparatus according to claim 2, wherein the controller is configured to determine a period between generation of synchronization signals based on the patient size characteristic input to the controller.

6. The ventilator apparatus according to claim 1, wherein the controller is configured to adjust the breath delivery parameters suitable for administering CPR to the patient based on a monitored ambient pressure.

7. The ventilator apparatus according to claim 1, wherein the periodic synchronization signal comprises at least a visual or audible signal to synchronize the performance of chest compressions.

8. The ventilator apparatus according to claim 1, wherein the controller is configured to increase the ventilation rate and to decrease the tidal volume when the assessed peak inspiratory pressure exceeds the predetermined threshold pressure.

9. The ventilator apparatus according to claim 1, wherein the controller is configured to readjust the ventilation rate and the tidal volume to reduce the peak inspiratory pressure and maintain the minute volume of the gas output to the patient's airway when the assessed peak inspiratory pressure remains above the predetermined threshold pressure after adjustment of the ventilation rate and the tidal volume.

10. The ventilator apparatus according to claim 1, wherein the controller is configured to generate an alarm after adjusting the ventilation rate and the tidal volume when the assessed peak inspiratory pressure remains above the predetermined threshold pressure.

11. The ventilator apparatus according to claim 1, wherein the two or more breath delivery parameters in the CPR tube mode comprise a ventilation rate of 10 ventilations per minute for an adult patient.

12. The ventilator apparatus according to claim 1, wherein the two or more breath delivery parameters in the CPR mask mode comprise delivery of two breaths to the patient after a predetermined period of chest compressions.

13. The ventilator apparatus according to claim 1, wherein the two or more breath delivery parameters in the CPR tube mode comprise an inspiration period to exhalation period ratio of 1:2.

14. The ventilator apparatus according to claim 1, wherein the two or more breath delivery parameters in the CPR mask mode comprise a repeating cyclic inspiration period to exhalation period ratio of 1:1 then 1:4.5.

15. The ventilator apparatus according to claim 1, wherein the two or more breath delivery parameters in the CPR mask mode comprise delivery of two breaths to the patient after a predetermined number of chest compressions.

16. A ventilator apparatus, comprising:
a portable housing;
a pneumatic assembly disposed in the portable housing, the pneumatic assembly being configured to output gas to be delivered to a patient's airway;
a controller disposed in the portable housing and in communication with the pneumatic assembly, the controller being configured to operate the pneumatic assembly to output gas to the patient's airway;
a barometric pressure sensor in communication with the controller, the barometric pressure sensor being configured to monitor ambient barometric pressure and to communicate the monitored ambient barometric pressure to the controller; and
at least one other sensor in communication with the controller and configured to take measurements with respect to the gas output to the patient's airway by the pneumatic assembly,
wherein the controller is configured to determine breathing parameter data and to operate the pneumatic assembly to output gas to the patient's airway according to the determined breathing parameter data, the breathing parameter data comprising a ventilation rate and a tidal volume,
wherein the controller is configured to determine an initial tidal volume based on a patient size characteristic input to the controller,
wherein the controller is configured to apply correction factors to the measurements made by the at least one other sensor in communication with the controller and to adjust the breathing parameter data based on the monitored ambient barometric pressure,
wherein the controller is configured to assess a peak inspiratory pressure of the gas output to the patient's airway and adjust the ventilation rate and the tidal volume to reduce the peak inspiratory pressure and maintain a desired minute volume of the gas output to the patient's airway when the assessed peak inspiratory pressure exceeds a predetermined threshold pressure,
wherein the at least one predefined operational mode comprises one or more CPR operational modes, the controller being configured to determine the breathing parameter data in accordance with the one or more CPR operational modes input to the controller, the one or more CPR operational modes comprising at least a CPR tube mode and a CPR mask mode,
wherein the controller is configured to receive a selection between the CPR tube mode and the CPR mask mode,
wherein the CPR tube mode is selected when the patient's airway requires the use of a tube device for ventilation and the CPR mask mode is selected when the patient's airway requires the use of a mask for ventilation, and
wherein the controller is configured to determine different breathing parameter data when the CPR tube mode is input to the controller than when the CPR mask mode is input to the controller.

17. The ventilator apparatus according to claim 16, wherein the controller is configured to determine the breathing parameter data in accordance with at least one other predefined operational mode input to the controller.

18. The ventilator apparatus according to claim 17, wherein the breathing parameter data determined by the controller in the one or more CPR operational modes is suitable for administering CPR to the patient.

19. The ventilator apparatus according to claim 18, wherein the controller is further configured to generate a periodic synchronization signal for a chest compression to be performed on the patient when administering CPR to the patient and to sequence, in a manner suitable for administering CPR to the patient, the generation of periodic synchronization signals with the operation of the pneumatic assembly to output gas to the patient's airway.

20. The ventilator apparatus according to claim 19, wherein the controller includes a metronome configured to generate the periodic synchronization signals.

21. The ventilator apparatus according to claim 19, wherein the controller is configured to determine a period between generation of synchronization signals based on at least one patient physical characteristic input to the controller.

22. The ventilator apparatus according to claim 17, further comprising at least one operator control disposed on the portable housing, the at least one operator control being configured to be manipulated to make inputs to the controller.

23. The ventilator apparatus according to claim 22, wherein the at least one operator control is configured to input at least one patient physical characteristic to the controller.

24. The ventilator apparatus according to claim 22, wherein the at least one operator control is configured to input the at least one predefined operational mode to the controller.

25. The ventilator apparatus according to claim 16, wherein the patient size characteristic comprises an estimated patient weight.

26. The ventilator apparatus according to claim 16, wherein the at least one other sensor comprises:
a first sensor disposed in or on the portable housing and configured to measure an output pressure of the gas output to the patient's airway by the pneumatic assembly and communicate the measured output pressure to the controller; and
a second sensor disposed in or on the portable housing and configured to measure a tidal volume of the gas output to the patient's airway by the pneumatic assembly and communicate the measured tidal volume to the controller,
wherein the controller is configured to operate the pneumatic assembly to adjust the output pressure and the tidal volume of the gas output by the pneumatic assembly based on the measured output pressure and the measured tidal volume such that the measured output pressure and the measured tidal volume correspond to an output pressure value and the tidal volume value of the breathing parameter data determined by the controller.

27. The ventilator apparatus according to claim 16, further comprising a manual breath control configured to be manipulated to command the controller to operate the pneumatic assembly to output at least one breath of gas to the patient's airway according to the breathing parameter data determined by the controller.

28. The ventilator apparatus according to claim 16, wherein the at least one other sensor comprises at least one pressure sensor.

29. The ventilator apparatus according to claim 28, wherein the at least one pressure sensor comprises a differential pressure transducer.

30. The ventilator apparatus according to claim 16, wherein the at least one other sensor comprises at least one flow sensor.

31. The ventilator apparatus according to claim 30, wherein the at least one flow sensor comprises at least one of an external air flow sensor or an external oxygen flow sensor.

32. The ventilator apparatus according to claim 16, wherein the controller is configured to increase the ventilation rate and to decrease the tidal volume when the assessed peak inspiratory pressure exceeds the predetermined threshold pressure.

33. The ventilator apparatus according to claim 16, wherein the controller is configured to determine if the patient is a child or adult based on the patient size characteristic input to the controller.

34. The ventilator apparatus according to claim 16, wherein the controller is configured to readjust the ventilation rate and the tidal volume to reduce the peak inspiratory pressure and maintain the minute volume of the gas output to the patient's airway when the assessed peak inspiratory pressure remains above the predetermined threshold pressure after adjustment of the ventilation rate and the tidal volume.

35. The ventilator apparatus according to claim 16, wherein the controller is configured to generate an alarm after adjusting the ventilation rate and the tidal volume when the assessed peak inspiratory pressure remains above the predetermined threshold pressure.

36. The ventilator apparatus according to claim 16, wherein the breathing parameter data in the CPR tube mode comprises a ventilation rate of 10 ventilations per minute for an adult patient.

37. The ventilator apparatus according to claim 16, wherein the breathing parameter data in the CPR tube mode comprises delivery of two breaths to the patient after a predetermined period of chest compressions.

38. The ventilator apparatus according to claim 16, wherein the breathing parameter data in the CPR tube mode comprises an inspiration period to exhalation period ratio of 1:2.

39. The ventilator apparatus according to claim 16, wherein the breathing parameter data in the CPR tube mode comprises a repeating cyclic inspiration period to exhalation period ratio of 1:1 then 1:4.5.

40. The ventilator apparatus according to claim 16, wherein the breathing parameter data in the CPR tube mode comprises delivery of two breaths to the patient after a predetermined number of chest compressions.

* * * * *